United States Patent [19]
Bodnaryk et al.

[11] Patent Number: 5,955,082
[45] Date of Patent: Sep. 21, 1999

[54] INSECTICIDAL FACTOR FROM FIELD PEAS

[75] Inventors: Robert P. Bodnaryk; Paul G. Fields; Yongshou Xie, all of Winnipeg; Kenneth A. Fulcher, Saskatoon, all of Canada

[73] Assignees: Her Majesty the Queen in right of Canada, as represented by Agriculture and Agri-Food Canada; Parrheim Foods, both of Canada

[21] Appl. No.: 08/790,986

[22] Filed: Jan. 29, 1997

[51] Int. Cl.$^6$ .................................................. A61K 35/78
[52] U.S. Cl. ........................................................ 424/195.1
[58] Field of Search .......................................... 424/195.1

[56] References Cited

FOREIGN PATENT DOCUMENTS 0 351 924   1/1990   European Pat. Off. .
WO 83 00419   2/1983   WIPO .

OTHER PUBLICATIONS

H.C.F. Su et al: Toxic effects of soybean saponin and its calcium salt on the rice weevil:, Journal of Economic Entomology, vol. 65, No. 3, 1972, College Park, Maryland, U.S., pp. 844–847, XP002065358, see p. 845, column 2, line–1–line 6.
Derwent Publications, Ltd. Database WPI: Section Ch, Week 7820; Class C03; AN78–35957A (XP002065359 & JP 53 038 626 A (Riken Koryo Kogyo K.).
Derwent Publications, Ltd. Database WPI: Section Ch, Week 8028; Class B04, AN80–49370C (XP002065360 & SU 698 623 A (Univ. Kish.).
The Effect of Yellow Split–Peas (*Pisum Sativum* L.) and Other Pulses on the Productivity of Certain Strains of *Sitophilus Oryzae* (L.) (Col. Curculionidae) and the Ability of Other Strains to Breed Thereon. C.W. Coombs et al., Ministry of Agriculture, Fisheries and Food, Pest Infestation Control Laboratory, London Road, Slough, Berks, England J. Stored Prod. Res. 1977, vol. 13, pp. 53–58, Pergamon Press, Printed in Great Britain.
The Potency and Effect of Phytotoxins Within Yellow Split–Pea (*Pisum sativum*) and adzuki bean (*Vigna angularis*) on survival and reproductive potential of *Sitophilus oryzae* (L.) (Coleoptera: Curculionidae) Graham, J. Holloway, Population Biology Laboratory, Department of Pure and Applied Zoology, University of Reading, Whiteknights, Reading, Berks, UK Bull. ent. Res. 76, pp. 287–295, Published 1986.
Toxins in Seeds E.A. Bell, Department of Plant Sciences, University of London, King's College, London, England, Biochemical Aspects of Plant and Animal Coevolution Proceedings of the Dhytochemical Soc. Symp. Reading, Apr. 1977, Harborne, J.B., pp. 143–161.

*Primary Examiner*—Jean C. Witz
*Attorney, Agent, or Firm*—Rothwell, Figg, Ernst & Kurz, P.C.

[57] ABSTRACT

A method and composition is provided to control insect pests using pea extracts. Pea extracts, protein-rich, fibre-rich and starch-rich fractions were tested for toxicity against various grain storage pests. The pea protein-rich extract was found to be toxic against the lesser grain borer, red flour beetle, rice weevil, maize weevil, granary weevil and the rusty grain beetle. The pea protein-rich extract also reduced the number of offspring of all insects tested. The protein-rich fraction was also found to be effective against the bertha army worm, diamondback, grasshopper, Indian meal moth and flea beetle. A partially purified active extract from the protein-rich fraction has been identified, using ion-exchange chromatography, reversed-phase chromatography, adsorption chromatography and gel filtration. However, the active ingredient within this fraction is not a protein with a molecular weight>above 4,000 daltons, nor is it a protease inhibitor, lectin or soyasaponin I.

13 Claims, 18 Drawing Sheets

INSECTICIDAL FACTOR FROM FIELD PEAS

The present invention relates to a method and composition to control insect pests using pea extracts.

BACKGROUND OF THE INVENTION

Insect pests cause heavy losses to stored grain, quantitatively and qualitatively (Sinha R. N. and Watters F. L. (1985), *Insect Pests of Flour Mills, Grain Elevators, and Feed Mills and Their Control*, Agriculture Canada, Publication 1776, p. 290; Madrid F. J., et al (1990), *Can. Ent.* 122, 515–523). Synthetic residual insecticides and fumigation are the main method of grain protection. However, increased public concern on the residual toxicity of insecticides applied to stored grain and the occurrence of insecticide-resistant insect strains are causing people to search for alternative methods to control insect pests.

It has long been known that legume seeds contain a wide range of chemicals with toxic or deterrent effects against insect pests (Harborne J. B., et al (1971), In *Chemotaxonomy of the Leguminosae*, Academic Press, London. p. 612; Bell E. A. (1978), Toxins in seeds, In *Biochemical Aspects of Plant and Animal Coevolution*, (Edited by Harborne J. B.) pp. 143–161, Academic Press, New York. p.435). The most common of these insect-active substances in the seeds of legumes are protease inhibitors (eg. the now classical soybean trypsin inhibitor), lectins of various specificities and a broad range of saponins. None of these substances, however, has been adapted commercially for controlling insects infesting grain. An admixture of yellow split-peas (*Pisum sativum*) with wheat resulted in a marked reduction of survival and reproduction of the rice weevil (*Sitopulus oryzae*) (Coombs C. W., et al (1977) *J. Stored Prod. Res.* 13, 53–58; Holloway G. J. (1986) *Bull. ent. Res.* 76, 287–295). These effects were achieved, however with admixtures containing equal weights of whole peas and wheat, and the method is not practical for controlling pests in grain that is being transported or stored.

Insect pests also cause heavy losses in various agricultural crops, including but not limited to canola and wheat.

There is thus a need to identify a component or fraction within a pea extract that can act as a natural insecticide against insects.

SUMMARY OF THE INVENTION

The present invention relates to a method and composition to control insect pests using pea extracts.

According to the present invention there is provided a bio-active ingredient from a pea extract which is effective in controlling insect pests, wherein said bio-active material is in a protein-rich fraction of the pea extract and is characterized as being alcohol-soluble, protease insensitive; and having a molecular weight of <4000 daltons; and wherein said bio-active material is shown to be distinct from other active bio-active substances in peas, including protease inhibitors, lectins and soyasaponin I.

BRIEF DESCRIPTION OF THE DRAWINGS

These and other features of the invention will become more apparent from the following description in which reference is made to the appended drawings wherein:

FIG. 8 shows the food preference of adult rusty grain beetle and rice weevil, to wheat kernels treated with various concentrations of pea protein or pea fibre.

DESCRIPTION OF PREFERRED EMBODIMENT

Figure 1A:
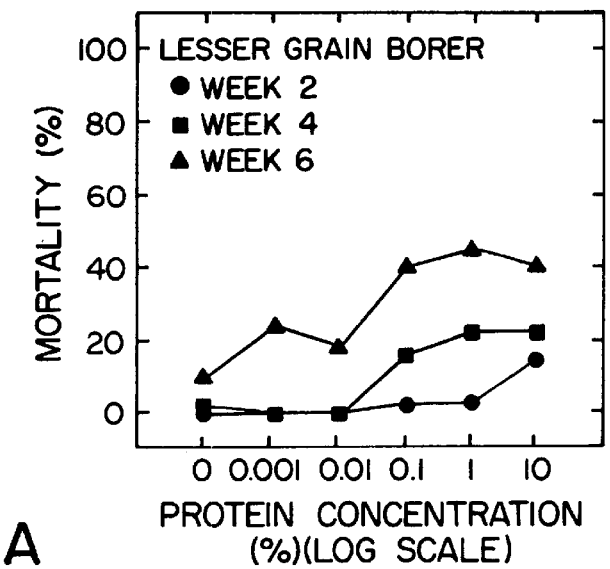
FIG. 1 shows the mortality of stored-products insects held on wheat kernels mixed with various concentrations of an air-classified protein fraction of peas. The insects are lesser grain borer (FIG. 1A), granary weevil (FIG. 1B), red flour beetle (FIG. 1C), maize weevil (FIG. 1D), rice weevil (FIG. 1E) and rusty grain weevil (FIG. 1F).
Figure 1B:
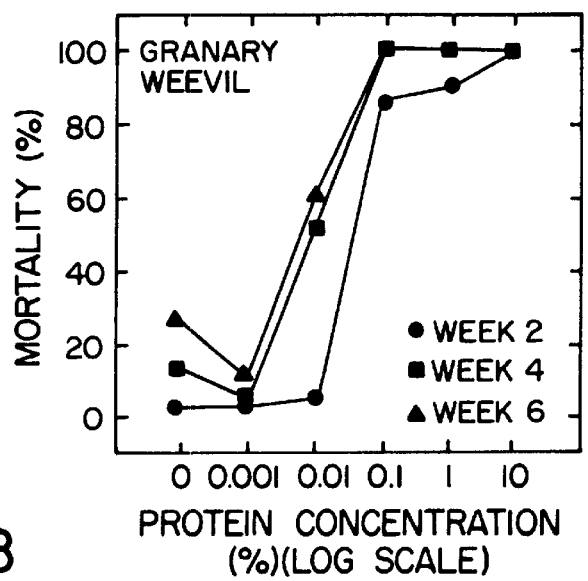
Figure 1C:
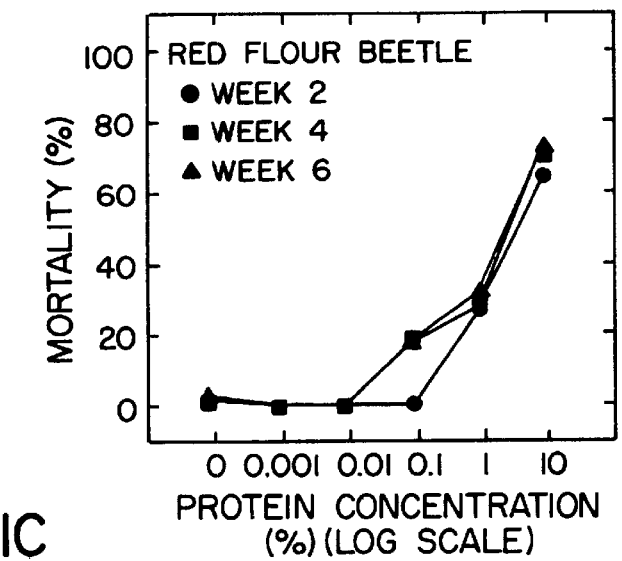
Figure 1D:
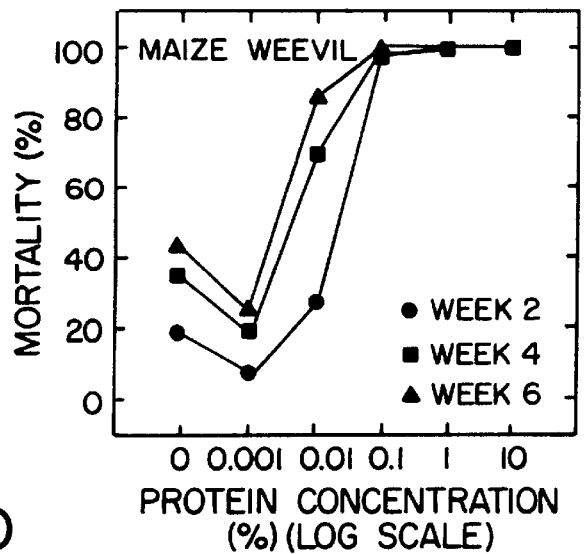
Figure 1E:
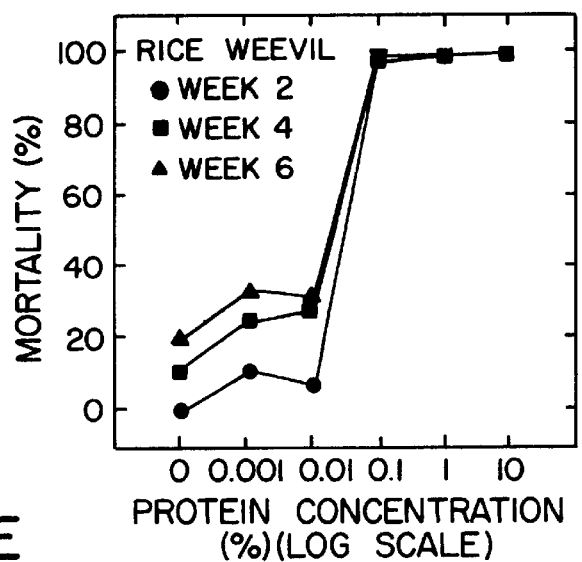
Figure 1F:
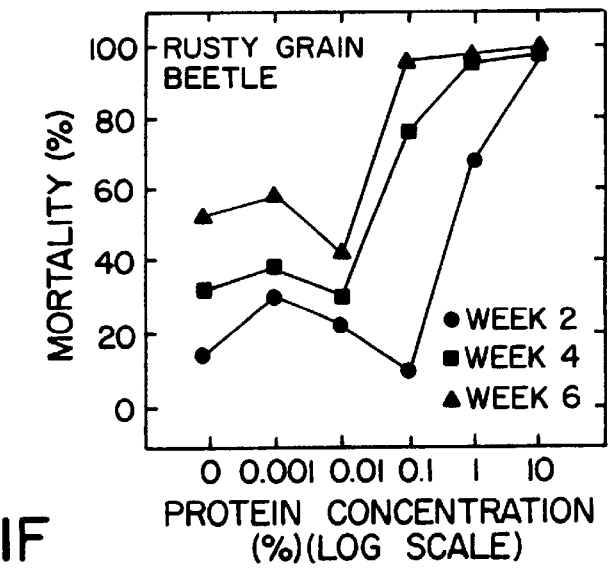

The present invention is directed to pea extracts which are effective in controlling insect pests. The pea extracts are selected from a protein-rich, a fibre-rich, and a starch-rich fraction.

According to the present invention, a number of methods were used to determine the effectiveness of the various pea extracts. For example, the mortality of a number of insects were determined when the insects were allowed to feed on the leaf disk, grain or flour from the grains treated with the pea extracts. Another indication of the effectiveness of the pea extracts was determined by studying the number of offspring from adult insects exposed to either grain or flour treated with the pea extracts. The repellant effect of the various pea extracts was also used to determined the effectiveness of the extracts. The extracts were mixed with either flour or the grains, and the insects were allowed by choice to feed on the treated material.

In the present invention, a variety of different insects were tested. Six species of stored-product insects (lesser grain borer Rhyzopertha dominica; granary weevil, Sitophilus granarius; maize weevil, S. zeamais; rice weevil, S. oryzae; red flour beetle, Tribolium castaneum; and rusty grain beetle, Cryptolestes ferrugineus) were tested with treated grain; and four species (flat grain beetle, Cryptolestes pusillus; flour mill beetle, Cryptolestes turcicus; red flour beetle; and confused flour beetle, Tribolium confusum) were tested with treated flour. These examples of stored-product insects were used as examples in the present invention and are not intended to limit the invention. In addition to the stored-product insects, the pea extracts were tested against Indian meal moth, flea beetle (Phyllotreta cruciferae), grasshoppers (Melanoplus sanguinipes), bertha army worm (Mamestra configurata) and diamondback (Plutella xylostella).

Of the three fractions tested, the protein-rich fraction was considered to be the most effective against the greatest number of insects. The fibre-rich fraction caused less mortality than the protein-rich fraction for a number of the insects tested. The starch-rich fraction showed no toxic effects on the adult insects, however, this fraction did reduce the number of offspring of the rusty grain beetle and the red flour beetle.

For the protein-rich fraction an effective concentration for treatment ranges from 0.01 to 10% weight/weight based on the grain or flour being treated by the protein-rich fraction, or 1 $\mu$g to 340 $\mu$g of pea extract per $cm^2$ of leaf or other plant surface. In one example of the present invention the concentration of the pea extract is from 17 to 90 $\mu$g/$cm^2$ of leaf or other plant surface. There was some variation depending upon the insect being tested. The most preferred concentration of protein-rich fraction can be determined empirically. The protein-rich fraction was thus chosen for further study and extraction to obtain a substantially purified active ingredient.

The protein-rich fraction can be used as a powder or can be dissolved in an aqueous medium, for example water. In the liquid application of the protein-rich fraction, 100 g of the protein-rich fraction was dissolved in 900 ml of water and was applied at a rate of 1 to 8% weight/weight. This is equivalent to from about 0.04 to about 0.32% of the protein-rich pea extract. Although the liquid application may in certain circumstances be preferred over the dry extract, it was found, in the examples of the present invention, not to be as active as the dry extract. Water is therefore not an efficient solvent for extracting the active ingredient from the protein-rich fraction.

The protein-rich fraction can be isolated from any type of pea, including commercial varieties and wild varieties. A number of pea varieties have been tested and all have been found to some extent to contain the active ingredient. There was, however, wide variation in the effectiveness of the pea extract depending upon the source of the extract, and a suitable variety can easily be determined empirically.

The protein-rich fraction, which contains the effective ingredient, was treated with heat and it was found that this heat treatment destroyed the activity. Thus, the active ingredient can be defined as being heat-sensitive.

In order to further define the active ingredient and to obtain a purified fraction thereof, the protein-rich fraction was subjected to purification steps as follows:

ammonium sulfate precipitation;

ion exchange chromatography; and gel filtration.

Ammonium sulfate was added from a concentration of 30 to 100 percent to obtain an ammonium sulfate precipitate. All of the fractions between 30 and 100 saturation with ammonium sulfate showed similar activity. For convenience, 90% ammonium sulfate precipitate was used in the purification procedure. The 90% ammonium sulfate precipitate was then further purified using ion exchange chromatography which separates material according to charge. The material was eluded from the column using a salt step gradient, with water, 0.5 M NaCl and 2.0 M NaCl. The active fraction from the ion exchange chromatography, which was eluted with water, was then further purified by gel filtration, which separates according to size. The active fraction isolated from the gel filtration column has an estimated molecular weight of <4000 daltons.

The active fraction as isolated from the gel filtration column was not sensitive to protease digestion, as determined using bromelin as a non-specific protease. Thus, although the term "protein-rich fraction" has been used throughout the present application, it does not imply that the active ingredient is a protein.

In a further embodiment of the present invention, the protein-rich fraction was also purified in a process involving solvent extraction. Following treatment with chloroform and alcohol, the active fraction was eluted from either a styrene-divinylbenzene copolymer resin (eg. DIAION HP20AG) resin, or a reversed phase column chromatography using a $C_8$ cartridge (eg. Sep-Pak Vac $C_8$) in the presence of methanol. This process results in an over 100 fold increase in the insecticidal efficacy of the active fraction.

Thus, according to the present invention, there is provided a bio-active ingredient from a pea extract which is effective in controlling insect pests in stored grains. The bio-active material can be defined a being present in a protein-rich fraction of the pea extract; heat-sensitive; protease insensitive; alcohol soluble; and having a molecular weight of <4000 daltons.

While this invention is described in detail with particular reference to preferred embodiments thereof, said embodiments are offered to illustrate but not limit the invention.

EXAMPLES

Example 1

Toxicity of a Protein-Rich, Fibre-Rich and Starch-Rich Pea Fraction Against Stored-Product Insects of Flour and Bulk Grain Pea extracts (protein-rich, fibre-rich and starch-rich fractions, commercially available from Parrheim Foods Ltd.) were taken out from storage (−20° C.) and mixed with Canada Western hard red spring wheat at concentrations of 0, 0.001, 0.01, 0.1, 1.0, and 10.0% (wt:wt). Wheat flour was treated at concentrations 0, 0.01, 0.1, 1.0, 10.0, 50.0, 100.0% (wt:wt). Approximately 20 grams of treated wheat kernels or flour were filled into glass vials (7 cm high, 2.7 cm diameter). Two sets of 5 vials were prepared for each treatment. Ten unsexed adult insects (7–14 days old) were introduced into each vial for the first set of vials (5 replicates). Six species of stored-product insect (lesser grain borer Rhyzopertha dominica; granary weevil, Sitophilus

*granarius*; maize weevil, *S. zeamais*; rice weevil, *S. oryzae*; red flour beetle, *Tribolium castaneum*; and rusty grain beetle, *Cryptolestes ferrugineus*) were tested with treated grain; and four species (flat grain beetle, *Cryptolestes fusillus*; flour mill beetle, *Cryptolest turcicus*; red flour beetle; and confused flour beetle, *Tribolium confusum*) were tested with treated flour. After 2 weeks at 30° C. and 70% R.H., adult insects were removed and placed in the second set of vials with the same treated kernels or flour. Mortality of adults was determined after 2, 4, and 6 weeks. The first set of vials were held in the incubator for an additional 5 weeks for a total of 7 weeks before counting offspring adults.

The pea protein-rich fraction was toxic to all insects tested (FIG. 1). As shown by the lethal concentration for 50% mortality of the population ($LC_{50}$) (Table 1) and FIG. 1, the weevils are the most sensitive of the insects tested, followed by the rusty grain beetle, the red flour beetle and the lesser grain borer was the most resistant insect. Note that the lower the $LC_{50}$ the less pea protein-rich fraction it takes to kill 50% of the population. Insects with a low $LC_{50}$ are sensitive to the pea protein-rich fraction.

TABLE 1

The $LC_{50}$ of adult insects exposed 2 weeks to wheat kernels treated with pea extracts. $LC_{50}$ is the lethal concentration for half the population. The 95% confidence interval means that there is a 95% chance that the $LC_{50}$ is with that range. $LC_{50}$ that have overlapping confidence intervals are not different.

| Pea extract | Insect species | $LC_{50}$ (%) | 95% confidence interval (%) |
|---|---|---|---|
| Protein | Rice Weevil | 0.02 | 0.01–0.04 |
|  | Maize Weevil | 0.03 | 0.01–0.05 |
|  | Granary Weevil | 0.06 | 0.03–0.14 |
|  | Rusty Grain Beetle | 0.14 | 0.03–0.68 |
| Fibre | Rusty Grain Beetle | 0.64 | 0.28–1.47 |

The pea protein-rich fraction also reduced the number of offspring of all insects tested (Table 2). $EC_{50}$ represent the concentrations needed to reduce treated populations to 50% of the untreated populations. For example a concentration of 0.16% pea protein-rich fraction is needed to reduce the offspring of the lesser grain borer to 50% of the untreated grain (Table 2). As with $LC_{50}$, the lower the $EC_{50}$ the more sensitive the insect is to the extract. Therefore the most sensitive insects are the rice weevil and the granary weevil, followed by the rusty grain beetle and the maize weevil. The offspring of red flour beetle and the lesser grain borer are the most resistant to the action of pea protein.

TABLE 2

Number of offspring developing in wheat kernels treated with pea extracts during a 7-week period.

|  | Protein | | | | | | Fibre | Starch |
|---|---|---|---|---|---|---|---|---|
| Concentration (%) | Lesser Grain Borer | Granary Weevil | Maize Weevil | Rice Weevil | Red Flour Beetle | Rusty Grain Beetle | Rusty Grain Beetle | Rusty Grain Beetle |
| 0 | 122 a[1] | 124 a | 97 a | 186 a | 7 b | 50 a | 49 a | 50 a |
| 0.001 | 119 ab | 114 ab | 131 a | 148 a | 12 a | 44 a | 59 a | 39 ab |
| 0.01 | 91 b | 82 b | 146 a | 123 a | 7 b | 38 a | 33 b | 31 bc |
| 0.1 | 53 c | 2 c | 4 b | 45 b | 6 b | 19 b | 26 b | 35 ab |
| 1.0 | 50 cd | 0 c | 0 b | 0.4 b | 2 c | 4 c | 78 c | 32 bc |
| 10.0 | 23 d | 0 c | 0 b | 0.3 b | 0.3 c | 0 d | 1 c | 17 |
| $EC_{50}$ (%)[2] | 0.16 | 0.018 | 0.065 | 0.020 | 0.22 | 0.039 | 0.074 | 0.036 |

[1]Means followed by the same letters within columns indicate no significant difference (P > 0.05) in LSD test.
[2]$EC_{50}$ represents effective concentration resulting in 50% reduction of offspring relative to controls at 0%.

Flour treated with the pea protein-rich fraction also caused mortality of insects (FIG. 3), but insects held on flour treated with the pea protein-rich fraction were less sensitive than insects held on grain (FIGS. 1, 3). For example, the red flour beetle held on kernels treated with 1% pea protein-rich fraction had over 20% mortality, whereas a similar treatment with flour produced no mortality. The flat grain beetle was the most sensitive insect, followed by the flour mill beetle and the confused flour beetle, with the red flour beetle being the most resistant.

Although pea protein-rich fraction did not kill adults to a great extent, it reduced offspring significantly (Table 3). Again the flat grain beetle is the most sensitive, followed by the confused flour beetle, with the red flour beetle offspring being the most resistant. As the flour mill beetle did not produce any offspring in the untreated flour we do not know what effects pea protein-rich fraction have on the offspring. The effects on the number of offspring could be through direct mortality of offspring, or a reduction of the parent population.

TABLE 3

Number of offspring developing in wheat flour treated with pea extracts during a 7-week period

| Concentration (%) | Protein | | | | Fibre | Starch |
|---|---|---|---|---|---|---|
| | Flat Grain Beetle | Flour Mill Beetle | Red Flour Beetle | Confused Flour Beetle | Confused Flour Beetle | Confused Flour Beetle |
| 0 | 17 b[1] | 0 a | 196 a | 180 a | 168 b | 173 ab |
| 0.01 | 26 a | 2 a | 194 a | 176 a | 197 a | 181 a |
| 0.1 | 9 c | 0.4 a | 200 a | 145 b | 175 b | 179 ab |
| 1.0 | 4 cd | 0.4 a | 164 b | 127 c | 163 b | 165 b |
| 10.0 | 0 d | 0.4 a | 113 c | 39 d | 88 c | 130 c |
| 50.0 | 0 d | 0 a | 6 d | 0 e | 14 d | 66 d |
| 100 | 0 d | 0 a | 0 d | 0 e | 0 d | 0 e |
| $EC_{50}$ (%)[2] | 0.58 | n.d.[3] | 2.12 | 1.13 | 2.84 | 5.55 |

[1]Means followed by the same letters within columns indicate no significant difference (P > 0.05) in LSD test.
[2]$EC_{50}$ represents effective concentration resulting in 50% reduction of offspring relative to controls.
[3]n.d. = Not determined.

Clearly the starch-rich fraction had no toxic effects on the adult red flour beetle (FIG. 3) or rusty grain beetle (FIG. 2), in fact it increased the survival of the rusty grain beetle. However, the starch-rich fraction did reduce the number of offspring of the rusty grain beetle (Table 2) and the red flour beetle (Table 3).

Figure 2A:
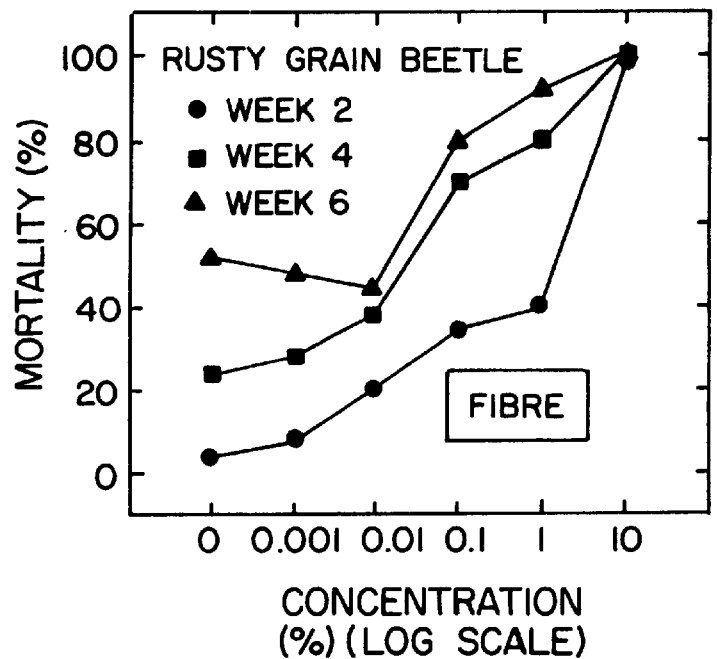
FIG. 2 shows the mortality of *C. ferrugineus* held on wheat kernels treated with various concentrations of the fibre (FIG. 2A) and starch (FIG. 2B) fraction of peas.
Figure 2B:
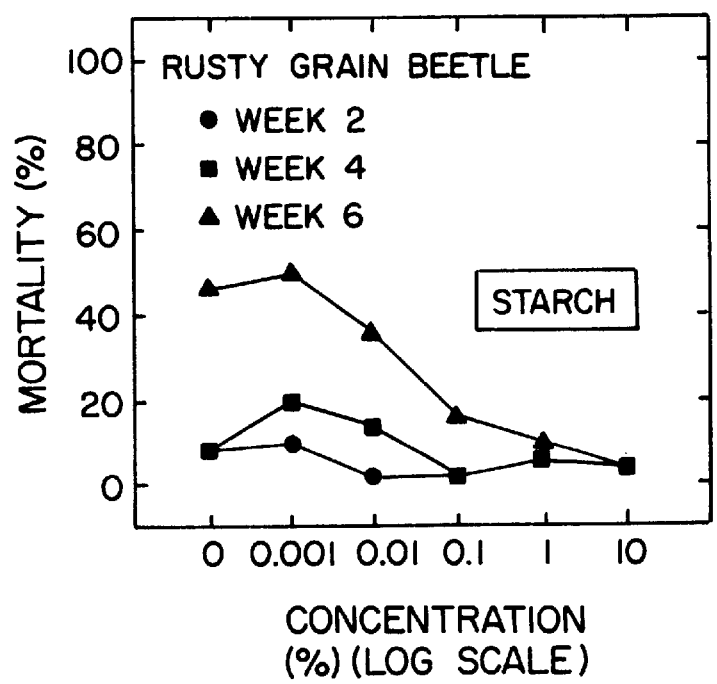
Figure 3A:
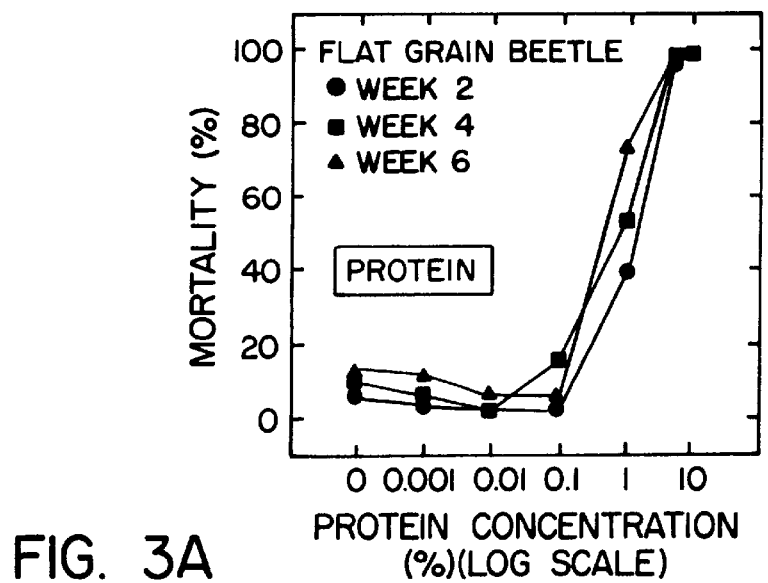
FIG. 3 shows the mortality of stored-products insects held on flour mixed with various concentrations of protein, fibre and starch fractions of peas. The insects are flat grain beetle (FIG. 3A), flour mill beetle (FIG. 3B), red flour beetle (FIG. 3C), confused flour beetle (FIG. 3D), confused flour beetle (FIG. 3E) and confused flour beetle (FIG. 3F).
Figure 3B:
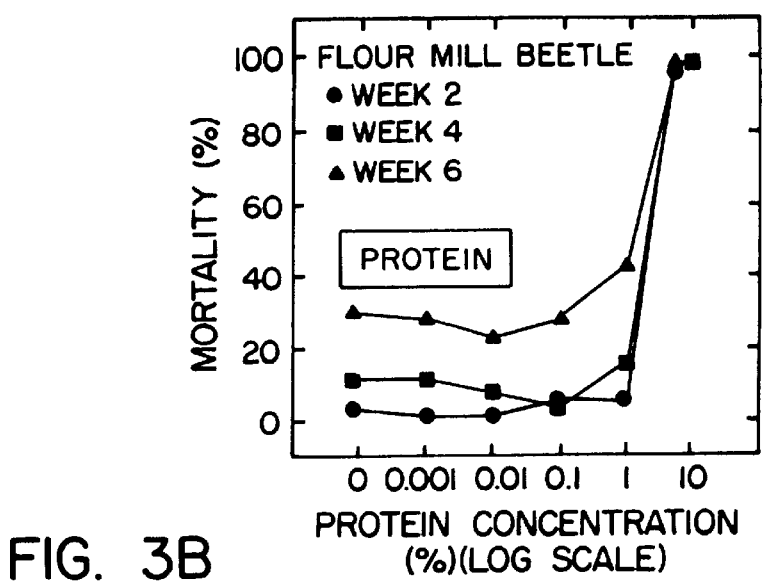
Figure 3C:
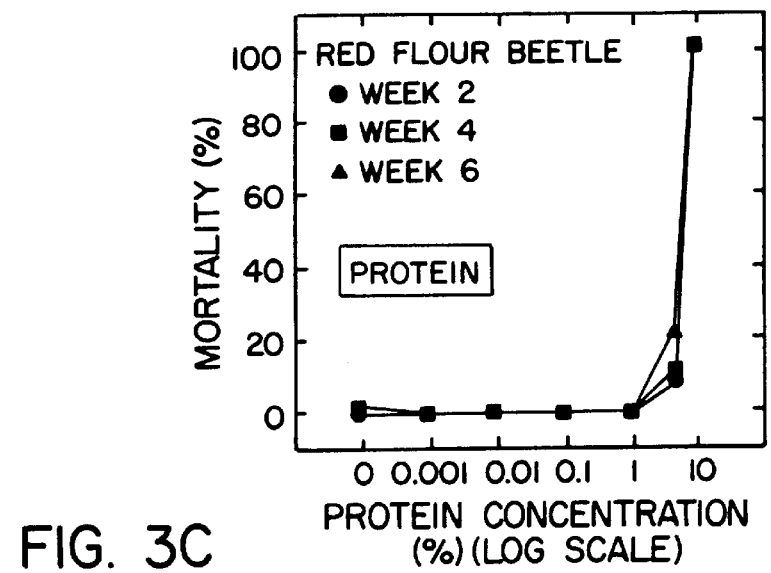
Figure 3D:
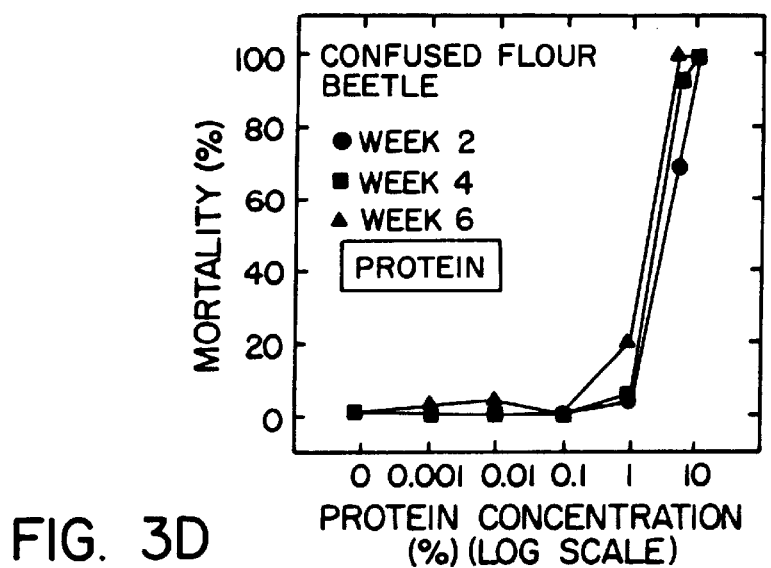
Figure 3E:
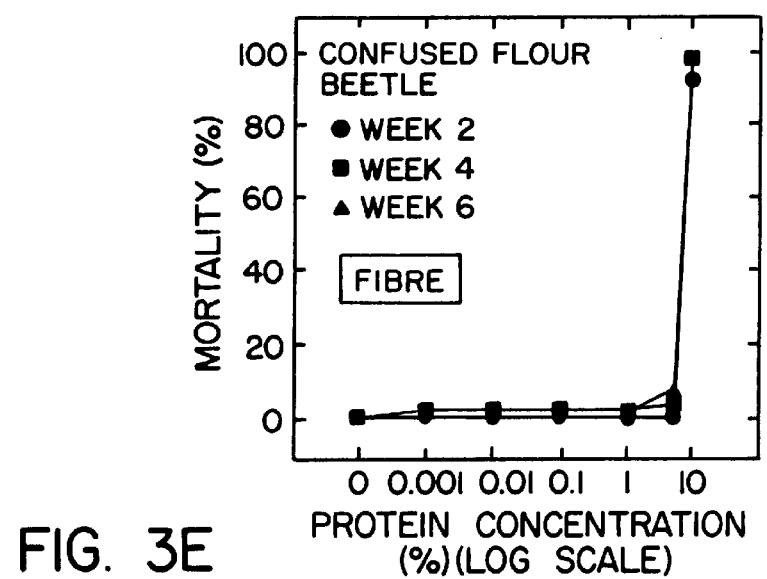
Figure 3F:
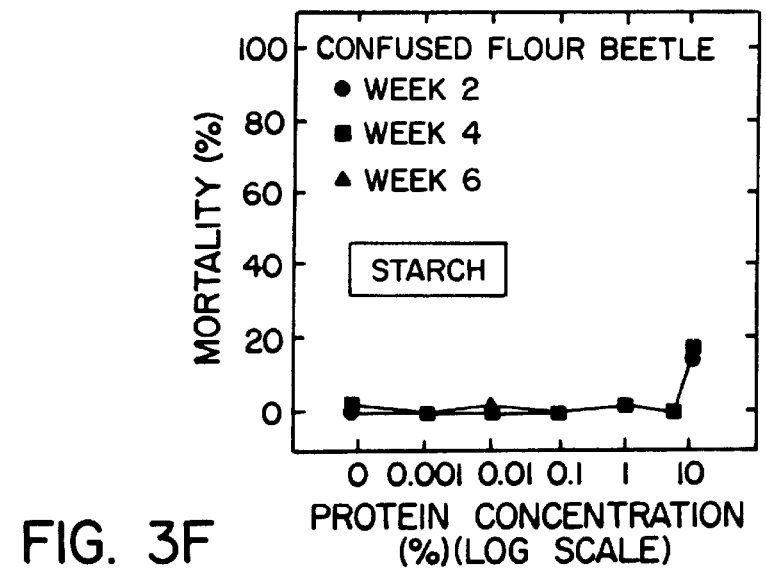

The fibre-rich fraction caused less mortality than the protein-rich fraction for the adult rusty grain beetle (FIGS. 1, 2, Table 1) and the confused flour beetle (FIG. 2). The offspring of the rusty grain beetle had similar response to the protein-rich and the fibre-rich fractions (Table 2). The offspring of the confused flour beetle were more effected by the protein-rich fraction than by the fibre-rich fraction (Table 3).

A pea protein-rich fraction extracted using the wet slurry technique (Woodstone) (Vose, J. R., 1980, Cereal Chemistry 57:406–410) was slightly less active than a protein-rich fraction prepared by Parrheim Foods, Saskatoon, SN Canada, using an air classification method (Tyler, R. T., Youngs C. G. and Sosulski F. W., 1981, American Association of Cereal Chemists 58:144–148) (Table 4).

TABLE 4

The mortality of the rice weevil when held on wheat mixed with pea protein from wet slurry extraction (Woodstone) and air classification extraction (Parrheim)[1]

| | Mortality (%) | | | | | |
|---|---|---|---|---|---|---|
| | Wet slurry days | | | Air classification days | | |
| Concentrations (%) | 7 | 15 | 21 | 7 | 15 | 21 |
| 0 | 0 | 2 | 8 | 6 | 6 | 12 |
| 0.001 | 0 | 0 | 4 | 2 | 6 | 8 |
| 0.01 | 0 | 4 | 6 | 2 | 32 | 46 |
| 0.1 | 48 | 94 | 100 | 40 | 100 | 100 |
| 1.0 | 46 | 94 | 100 | 88 | 100 | 100 |
| 10 | 54 | 100 | 100 | 98 | 100 | 100 |

[1]Five replicates with 10 insects/rep.

To study stability of bioactivity pea extracts against stored-product insects, treated grain and flour as described above were kept in an incubator at 30° C. and 70% R.H. for 8 months, and toxicity test was conducted as previously described.

It was found that insecticidal activity of pea extracts was reduced after treated wheat grain and flour were kept incubator for 8 months (Table 5, 6). For instance, new protein-treated wheat grain (at 0.1%) caused rice weevil 98%, 100%, and 100% mortality after 2 weeks, 4 weeks and 6 weeks exposure, respectively; while old protein-treated wheat grain caused rice weevil 10%, 18%, and 40% mortality at week 2, week 4, and week 6, respectively (Table 5). Since a high mortality with control (0%) for rusty grain beetle, we cannot compare old and new pea extracts (Table 5). New protein-treated flour (at 50%) caused 70%, 94%, and 100% mortality of confused flour beetle at week 2, week 4, and week 6, respectively; while old protein-treated flour caused confused flour beetle 38%, 74%, and 94% mortality at week 2, week 4, and week 6, respectively (Table 6). Both new and old fibre-treated flour remained similar activity against confused flour beetle (Table 6).

TABLE 5

The stability of pea extracts:
Mortality of adults from wheat kernels treated with pea extracts.

| | | Mortality (%) | | | | | | |
|---|---|---|---|---|---|---|---|---|
| | | Rusty Grain Beetle | | | | | Rice Weevil | |
| Duration | Concentration | Protein | | Fibre | | Starch | Protein | |
| (weeks) | (%) | Old[1] | New[2] | Old | New | Old | New | Old | New |
| 2 | 0 | 30 | 14 | 30 | 4 | 52 | 2 | 2 | 0 |
| | 0.001 | 38 | 30 | 62 | 8 | 54 | 4 | 4 | 12 |
| | 0.01 | 2 | 22 | 62 | 20 | 12 | 8 | 8 | 8 |
| | 0.1 | 52 | 10 | 22 | 34 | 20 | 10 | 10 | 98 |
| | 1 | 28 | 68 | 4 | 40 | 2 | 66 | 66 | 100 |
| | 10 | 92 | 98 | 12 | 98 | 8 | 60 | 60 | 100 |
| 4 | 0 | 94 | 32 | 48 | 24 | 86 | 12 | 12 | 12 |
| | 0.001 | 66 | 38 | 92 | 28 | 76 | 16 | 16 | 26 |
| | 0.01 | 2 | 30 | 74 | 38 | 80 | 20 | 20 | 28 |
| | 0.1 | 98 | 76 | 70 | 70 | 64 | 78 | 18 | 100 |
| | 1 | 76 | 96 | 22 | 80 | 16 | 100 | 100 | 100 |
| | 10 | 100 | 98 | 82 | 100 | 8 | 100 | 100 | 100 |
| 6 | 0 | 96 | 52 | 56 | 52 | 88 | 14 | 14 | 20 |
| | 0.001 | 68 | 58 | 94 | 48 | 78 | 26 | 26 | 34 |
| | 0.01 | 74 | 42 | 86 | 44 | 80 | 40 | 40 | 32 |
| | 0.1 | 98 | 96 | 78 | 80 | 44 | 50 | 50 | 100 |
| | 1 | 78 | 98 | 34 | 92 | 22 | 100 | 100 | 100 |
| | 10 | 100 | 100 | 94 | 100 | 12 | 100 | 100 | 100 |

[1] Old pea extracts were placed on wheat grain and kept in incubator at 30° C. and 70% R.H. for 8 months before use.
[2] New pea extracts were placed directly on grain from pure extracts stored at −20° C.

TABLE 6

The stability of pea extracts:
Mortality of adults from wheat flour treated with pea extracts.

| | | Mortality (%) | | | | | | |
|---|---|---|---|---|---|---|---|---|
| | | Confused Flour Beetle | | | | | Red Flour Beetle | |
| Duration | Concentration | Protein | | Fibre | | Starch | Protein | |
| (weeks) | (%) | Old[1] | New[2] | Old | New | Old | New | Old | New |
| 2 | 0 | 0 | 0 | 0 | 0 | 8 | 0 | 0 | 0 |
| | 0.01 | 0 | 0 | 6 | 0 | 2 | 0 | 4 | 0 |
| | 0.1 | 0 | 2 | 2 | 0 | 0 | 0 | 2 | 0 |
| | 1 | 4 | 0 | 0 | 0 | 4 | 0 | 6 | 0 |
| | 10 | 4 | 4 | 2 | 0 | 0 | 2 | 8 | 0 |
| | 50 | 38 | 70 | 4 | 0 | 0 | 0 | 0 | 8 |
| | 100 | 100 | 100 | 98 | 98 | 2 | 14 | 100 | 100 |
| 4 | 0 | 0 | 0 | 0 | 0 | 12 | 2 | 0 | 2 |
| | 0.01 | 2 | 0 | 6 | 2 | 4 | 0 | 6 | 0 |
| | 0.1 | 0 | 0 | 4 | 2 | 0 | 0 | 4 | 0 |
| | 1 | 6 | 0 | 0 | 2 | 4 | 0 | 6 | 0 |
| | 10 | 10 | 6 | 2 | 2 | 2 | 2 | 10 | 0 |
| | 50 | 74 | 94 | 4 | 4 | 4 | 0 | 2 | 12 |
| | 100 | 100 | 100 | 100 | 100 | 2 | 18 | 100 | 100 |
| 6 | 0 | 0 | 0 | 4 | 0 | 12 | 2 | 0 | 2 |
| | 0.01 | 6 | 2 | 8 | 2 | 4 | 0 | 8 | 0 |
| | 0.1 | 0 | 4 | 4 | 2 | 0 | 2 | 8 | 0 |
| | 1 | 6 | 0 | 0 | 2 | 6 | 0 | 6 | 0 |
| | 10 | 30 | 20 | 16 | 2 | 10 | 2 | 12 | 0 |
| | 50 | 94 | 100 | 60 | 8 | 12 | 0 | 14 | 22 |
| | 100 | 100 | 100 | 100 | 100 | 12 | 18 | 100 | 100 |

[1] Old pea extracts were placed on wheat grain and kept in incubator at 30° C. and 70% R.H. for 8 months before use.
[2] New pea extracts were placed directly on grain from pure extracts stored at −20° C.

Table 7 shows comparative results of effect of new and old pea extract-treated grain on offspring. Generally, after 8 months kept in incubator (30° C., 70% R.H.), reproduction inhibiting effect of pea extracts was reduced compared with new treated grain (Table 7). However, the reproduction inhibiting effect of both new and old pea extract-treated flour was the same (Table 8).

TABLE 7

The stability of pea extracts: Offspring from wheat kernels treated with pea extracts.

| Concen-tration (%) | Rusty Grain Beetle | | | | | | Rice Weevil | |
|---|---|---|---|---|---|---|---|---|
| | Protein | | Fibre | | Starch | | Protein | |
| | Old[1] | New[2] | Old | New | Old | New | Old | New |
| 0.0 | 17 | 50 | 18 | 50 | 10 | 50 | 233 | 186 |
| 0.001 | 16 | 44 | 11 | 59 | 18 | 39 | 230 | 148 |
| 0.01 | 12 | 38 | 8 | 33 | 49 | 31 | 237 | 123 |
| 0.1 | 14 | 19 | 35 | 26 | 48 | 35 | 253 | 45 |
| 1.0 | 13 | 4 | 40 | 8 | 37 | 32 | 80 | 0 |
| 10.0 | 2 | 0 | 26 | 1 | 10 | 17 | 63 | 0 |

[1]Old pea extracts were placed on wheat grain and kept in incubator at 30° C. and 70% R.H. for 8 months before use.
[2]New pea extracts were placed directly on grain from pure extracts stored at −20° C.

TABLE 8

The stability of pea extracts: Offspring from wheat flour treated with pea extracts.

| Concen-tration (%) | Confused Flour Beetle | | | | | | Red Flour Beetle | |
|---|---|---|---|---|---|---|---|---|
| | Protein | | Fibre | | Starch | | Protein | |
| | Old[1] | New[2] | Old | New | Old | New | Old | New |
| 0.0 | 133 | 180 | 136 | 168 | 134 | 173 | 197 | 196 |
| 0.01 | 120 | 176 | 120 | 197 | 138 | 181 | 181 | 194 |
| 0.1 | 124 | 146 | 129 | 175 | 105 | 179 | 179 | 200 |
| 1 | 86 | 127 | 125 | 163 | 134 | 165 | 185 | 164 |
| 10 | 14 | 39 | 73 | 88 | 95 | 130 | 79 | 113 |
| 50 | 0 | 0 | 8 | 14 | 28 | 66 | 21 | 6 |
| 100 | 0 | 0 | 0 | 0 | 1 | 0 | 0 | 0 |

[1]Old pea extracts were placed on wheat grain and kept in incubator at 30° C. and 70% R.H. for 8 months before use.
[2]New pea extracts were placed directly on grain from pure extracts stored at −20° C.

Example 2

The Repellent Effect of Pea Extracts against Stored Product Insect Pests

The repellent effect of pea extracts (protein-rich, fibre-rich, and starch-rich fractions) was tested against three species of stored product insect pests, the rusty grain beetle, the rice weevil, and the red flour beetle.

Pea extracts (protein, fibre and starch as obtained in Example 1) were mixed with Canada Western hard red spring wheat at concentrations of 0, 0.001, 0.01, 0.1, 1.0, and 10.0% (wt:wt). After mixing by hand, jars were rotated on a barrel roller for 10 minutes to obtain uniform treatment distribution. Food preference chambers (Loschiavo S. R. (1952), *Cereal Chem.* 29, 91–107) were used to conduct multiple choice bioassay. The chamber was a cylindrical brass (6 cm high, 30 cm diameter), with raised arena (2 cm high, 10 cm diameter) in the centre of the chamber. It was divided into 6 equal sections by brass partitions. Six sections were filled with 200-g treated wheat grains. Sections were randomly selected. Two hundred unsexed adult beetles (1–2 week old) were introduced into the centre of the arena, confined by a brass ring (2.5 cm high, 5 cm diameter), and then, a circular black-painted plate was covered to the top of the chamber. After 1 h confinement, which should be sufficient time for beetles to return to normal activity (Loschiavo, 1952, op cit.), beetles were released by raising up the brass ring without interrupting their activity. The chamber was kept in a growth incubator at 30° C. and 70% R.H. for 48 hrs. At the end of 48 hrs, the contents of each sections were vacuumed individually and the number of beetles counted. The whole experiment was repeated four times.

Figure 4A:
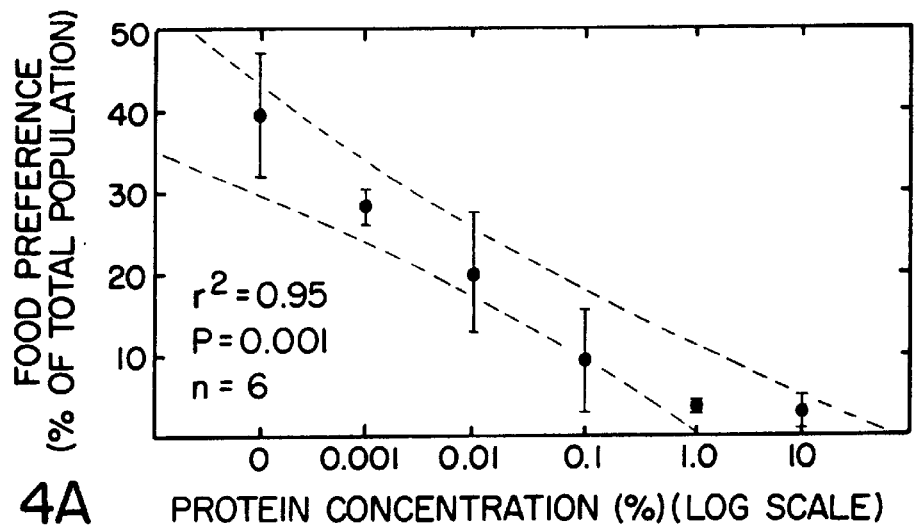
FIG. 4 shows the food preference of adult rusty grain beetle (FIG. 4A), rice weevil (FIG. 4B), and red flour beetle (FIG. 4C) to wheat kernels treated with various concentrations of pea protein under multiple choice condition.

Wheat treated with pea protein repelled both rusty grain beetle and rice weevil. When wheat was treated with the pea protein-rich fraction at concentrations 10.0%, they reduced insect food preference by 93% for rusty grain beetle, and 90% for rice weevil, compared with controls. Adults of red flour beetle were not repelled by pea protein (FIG. 4C).

Figure 5A:
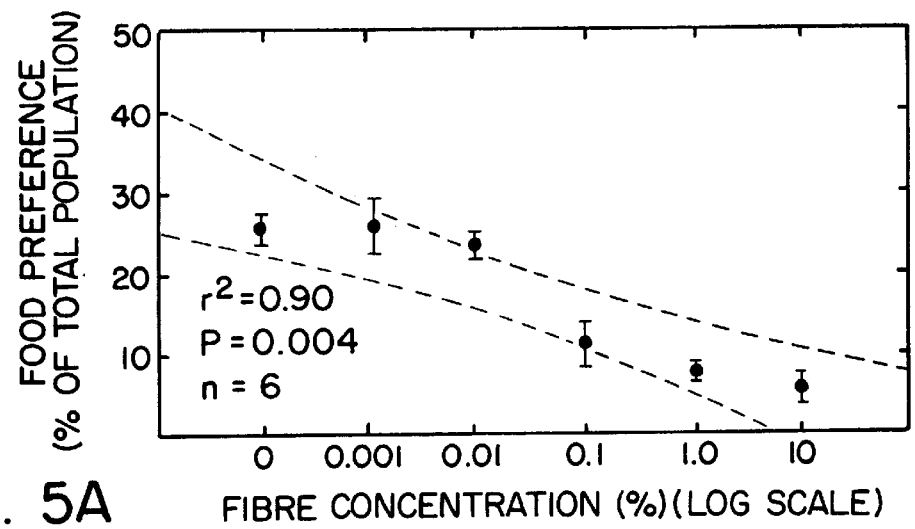
FIG. 5 shows the food preference of adult rusty grain beetle (FIG. 5A), rice weevil (FIG. 5B), and red flour beetle (FIG. 5C) to wheat kernels treated with various concentrations of pea fibre under multiple choice conditions.
Figure 5B:
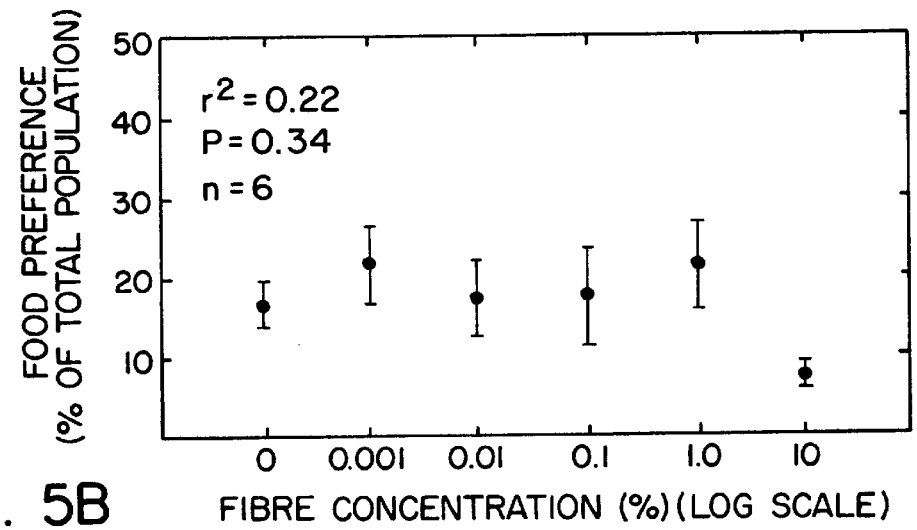
Figure 6A:
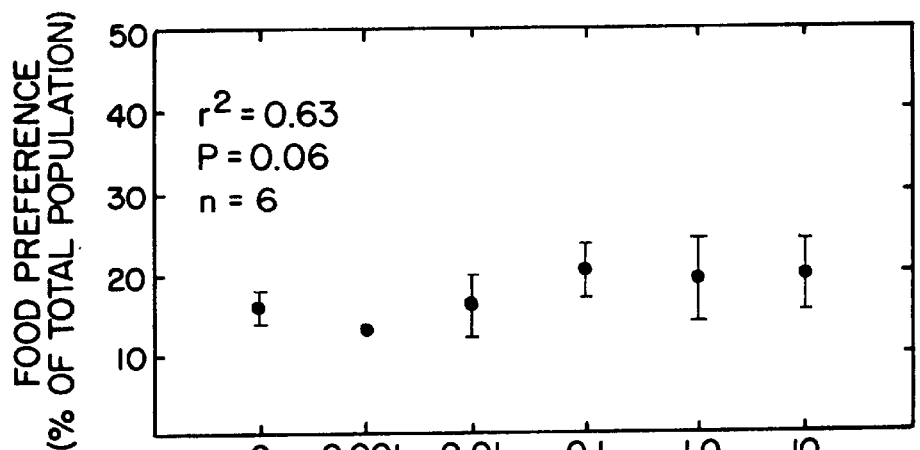
FIG. 6 shows the food preference of adult rusty grain beetle (FIG. 6A), rice weevil (FIG. 6B), and red flour beetle (FIG. 6C) to wheat kernels treated with various concentrations of pea starch under multiple choice condition.
Figure 6B:
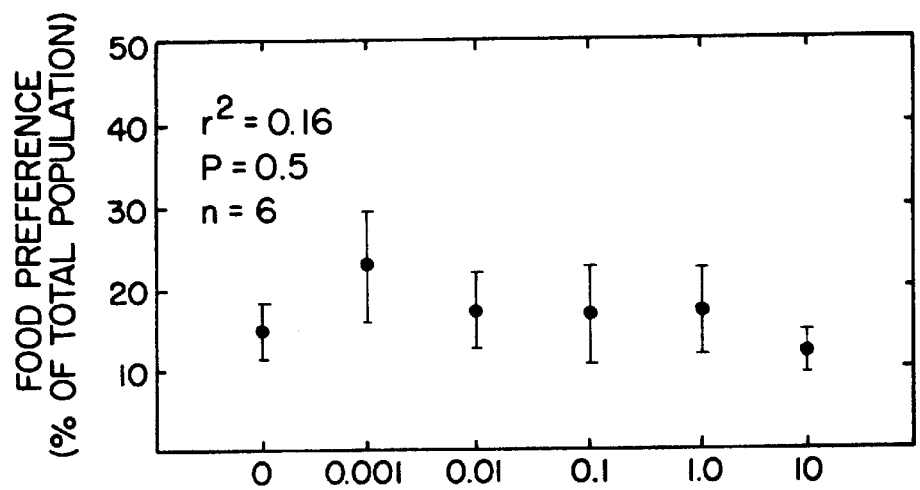
Figure 6C:
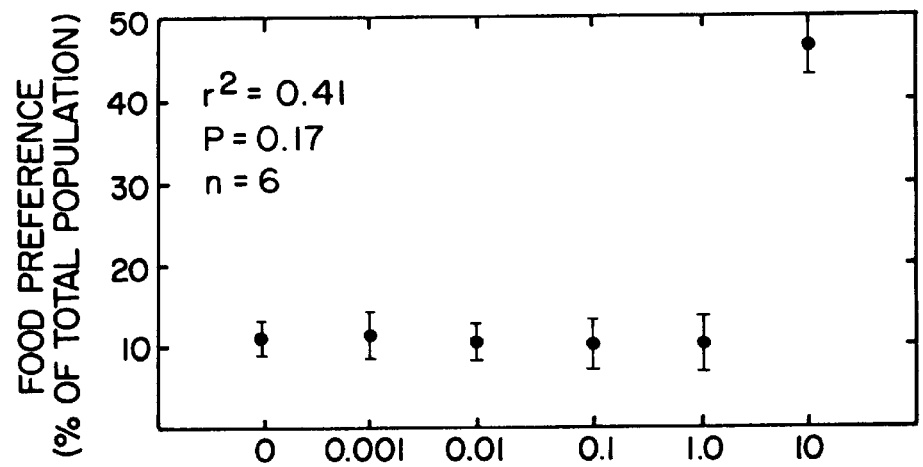

Adults of rusty grain beetle were also repelled by the pea fibre-rich fraction. The number of insects per section was negatively correlated with pea fibre concentration (FIG. 5A), with there be 78% fewer insects at 10% pea fibre than controls. In contrast, both rice weevil and red flour beetle were not repelled by pea fibre-rich fraction (FIGS. 5B, C). The pea starch-rich fraction did not show any repellent effect on the three insect species tested (FIG. 6).

Figure 4B:
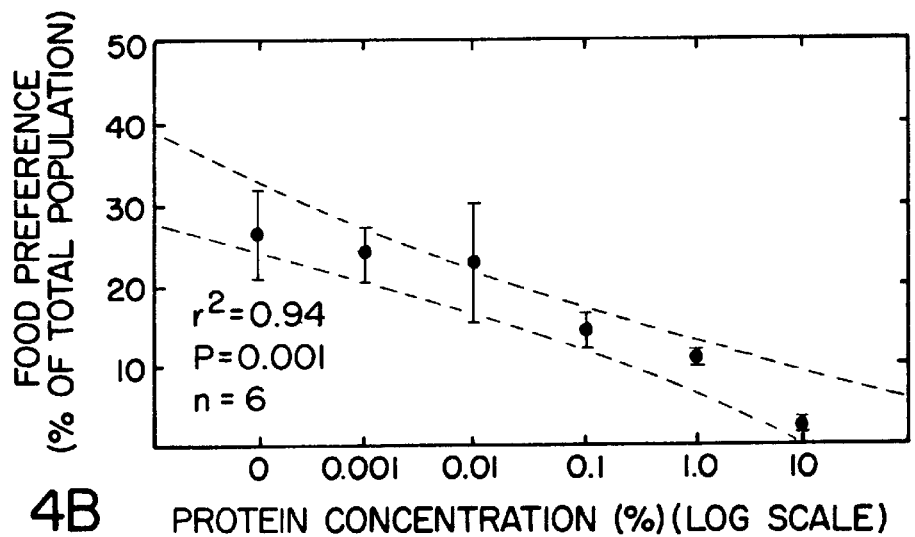
Figure 4C:
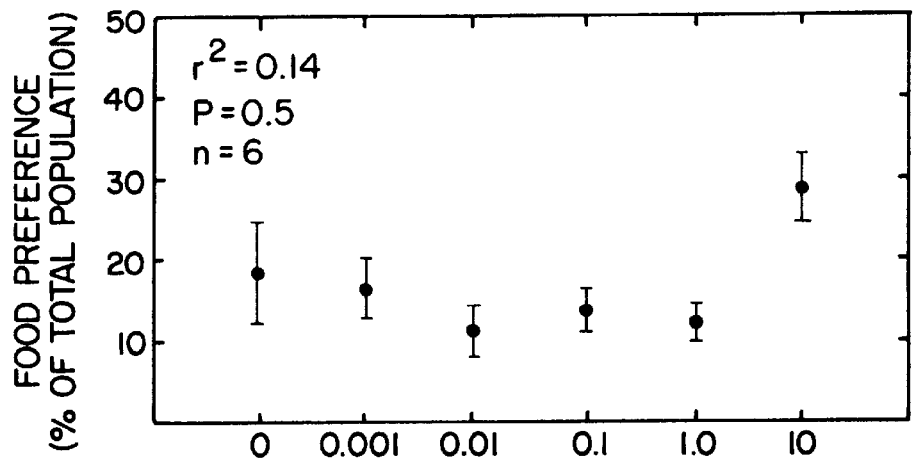
Figure 5C:
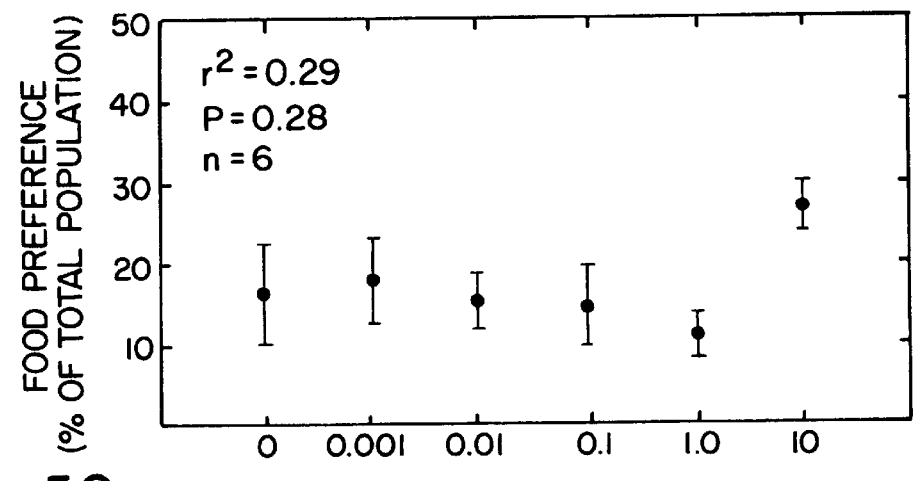

The repellent effect of pea extracts was reflected by the fact that the number of insect in treated area decreased as the concentration increased (FIGS. 4 and 5). With certain test materials, various insect species reacted differently. Our study indicated that rusty grain beetle was the most sensitive species to the repellent action, and then in decreasing order of rice weevil and red flour beetle. The pea protein-rich fraction was the most repellent to stored-product insect pests. This was consistent with our earlier observations that protein fraction was the most active one (compared with fibre and starch) in causing insect mortality and reducing insect progeny. Over all, the present study clearly indicates that insect preference (food acceptability) was reduced.

The mortality and repellance are linked in that highly toxic concentrations are also highly repellant. Significant correlations between toxic effect (mortality) (Example 1) and repellent effect (FIGS. 4A and B; FIG. 5A) were found for protein vs. rusty grain beetle ($r^2=0.80$, P=0.04), protein vs. rice weevil ($r^2=0.84$, P=0.1), and fibre vs. rusty grain beetle ($r^2=0.70$, P=0.04).

In order to test the sensitivity of insects to the repellent effect of pea extracts, two separate multiple choice tests, one based on insect age and another on exposure time, were conducted with the pea protein-rich fraction and rusty grain beetle. Four age classes of insects: <1 week-old, 1–2 week-old, 3–4 week-old, and 5–6 week-old were used. All test procedures were identical as described above. To test the rapidity of response, two hundred unsexed adult beetles (1–2 week old) were introduced into the test chamber, and counted at 0.5, 1, 2, or 4 h. Four replicates were used for each experiment.

Linear regression analysis was applied to define all dose-response relationships when correlation was found to be significant. A log (x+0.0001) transformation was performed before the regression analysis (where x=pea extract concentration). Analysis of covariance (ANCOVA) was used to test differences between of regression coefficients (Zar, J. H., 1984, Biostatistical Analysis. Prentice Hall, Englewood Cliffs, N.J. 718 pp.).

The age of rusty grain beetles did not affect the repellency of pea protein, and ANCOVA indicated that all slopes were not significantly different (P>0.05) (F=0.15, $F_{0.05(1),3,6}$= 3.24).

Figure 7A:
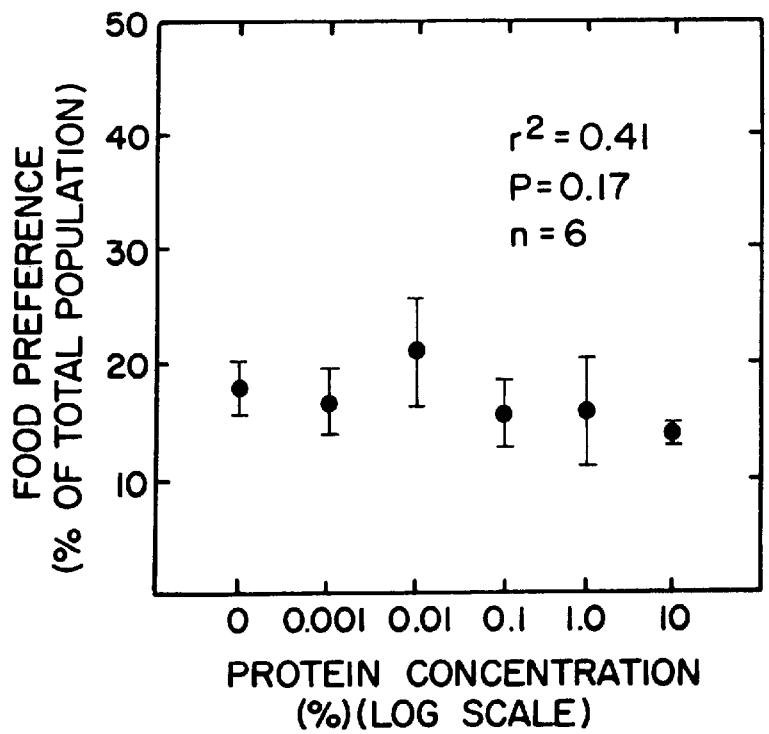
FIG. 7 shows the food preference of adult rusty grain beetle on wheat kernels treated with various concentrations of pea protein after 0.5 h (FIG. 7A), 1 h (FIG. 7B), 2 h (FIG. 7C), and 4 h (FIG. 7D) exposure under multiple choice conditions.
Figure 7B:
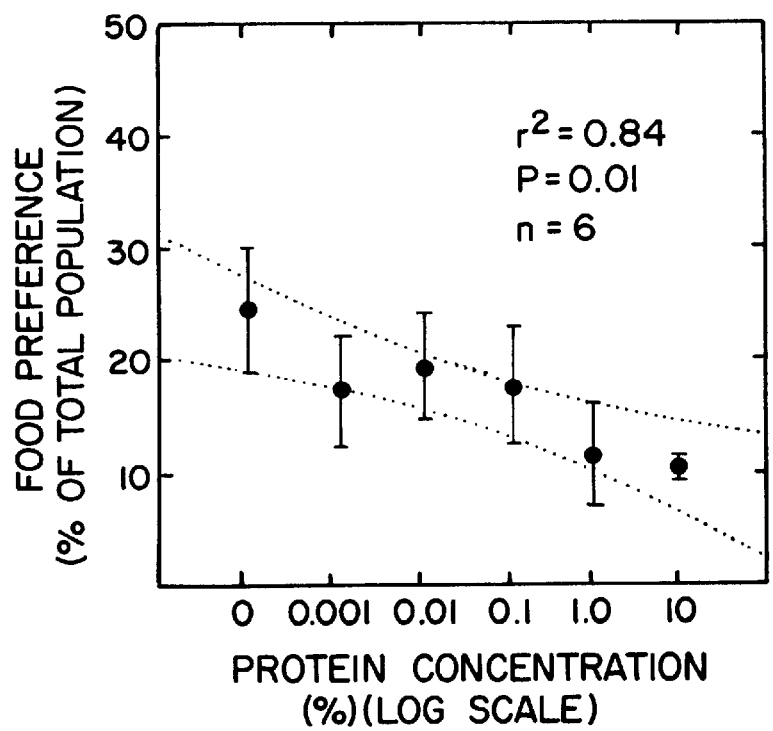
Figure 7C:
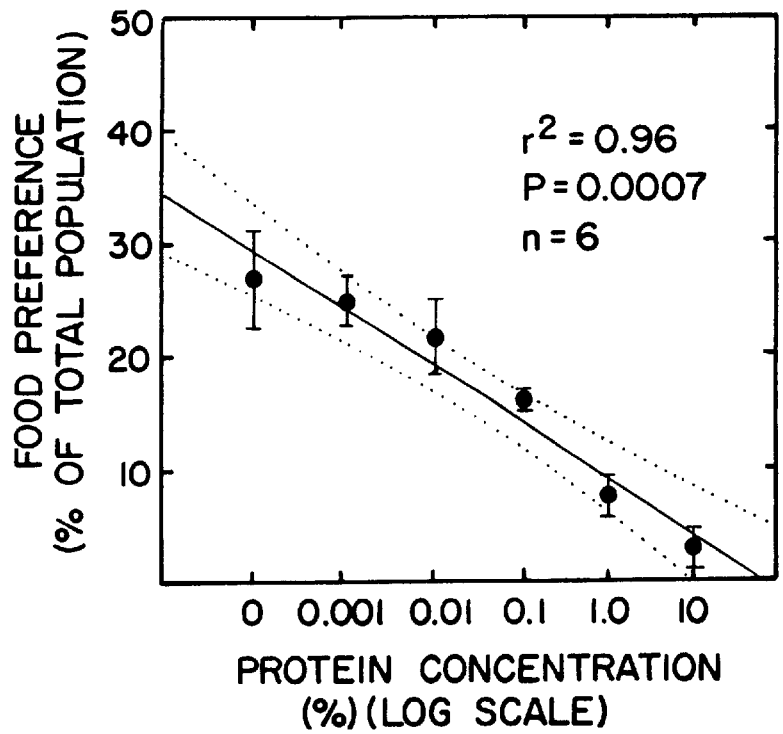
Figure 7D:
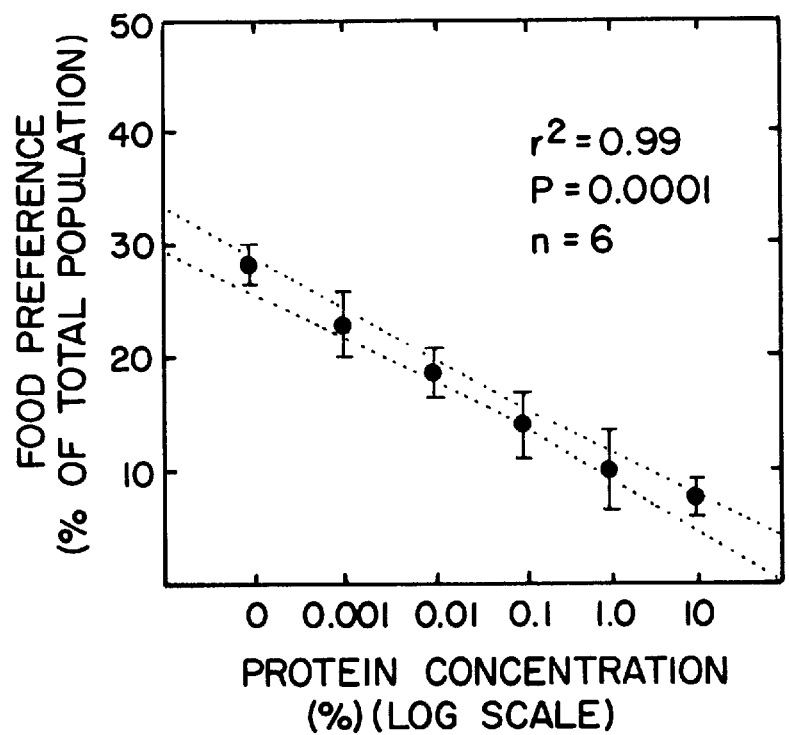

The repellency of pea protein against rusty grain beetle occurred even after 1 h exposure (FIG. 7B). ANCOVA indicated that slopes after 1, 2, and 4 h exposure were not significantly different (P>0.05) (F=1.47, $F_{0.05(1),2,12}$=3.89), although the linear relationship was increased as exposing time increased (FIGS. 7B, C and D). After half hour exposure to pea protein-treated wheat kernels, adults rusty grain beetle were almost equally distributed in all sectors (FIG. 7A).

Generally, response of insects to activity of chemical substances, either repellency, deterrency, or toxicity, is associated with insect age, i.e. the younger they are, the more sensitive they react. However, it was not the case with the pea protein-rich fraction vs. rusty grain beetle (Table 9). An equal repellent activity was observed against rusty grain beetle no matter at what age from <1 to 6 week-old (FIG. 7). This aspect, as well as the fact that the repellent action of the pea protein-rich fraction occurred after insects exposed to as short as 1 h (FIG. 7B), could improve the effectiveness of this material in practical use.

Habituation of insects to repellents or antifeedants is one of the major problems concerning their practical application (Schoonhoven L. M., (1982), *Ent. Exp. & Appl.* 31, 57–69); Jermy T., (1990), *J. Chem. Ecol.* 16, 3151–3166). To test if stored-product insects would become habituated to pea extracts, approximately one thousand adult rusty grain beetle (1–2 week-old) and rice weevil (1–2 week-old) were placed on 3 kg wheat kernels treated with 0.01% protein, or 0.01% fibre (for rusty grain beetle only) for 4 weeks at 30±1° C., 70±5% R.H. This concentration (0.01%) was selected because it caused ca. 20% mortality for both species (Example 1), and also showed repellent effects. After 4 weeks the insects were shaken out and used for a multiple choice test as mentioned above.

Figure 8A:
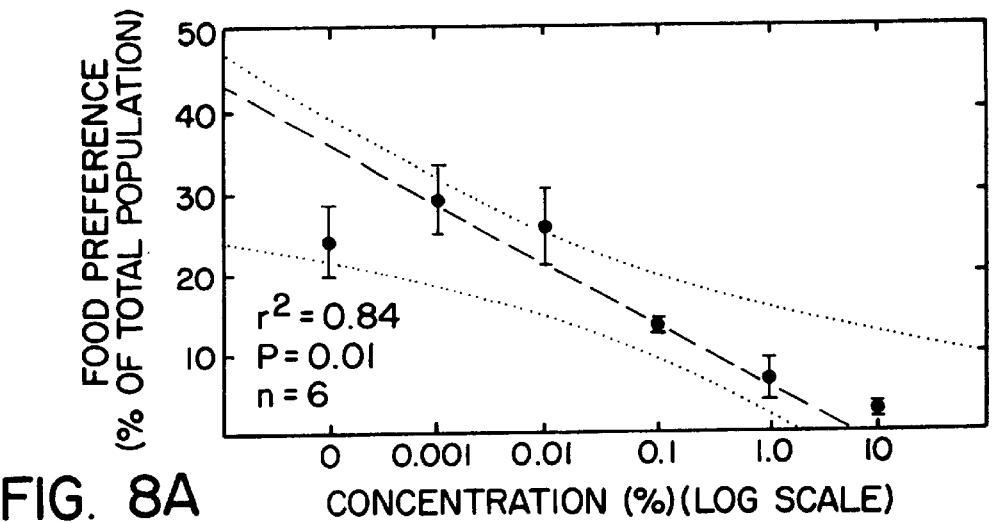
FIG. 8A shows the results of rusty grain beetle and wheat kernels treated with pea protein.
Figure 8B:
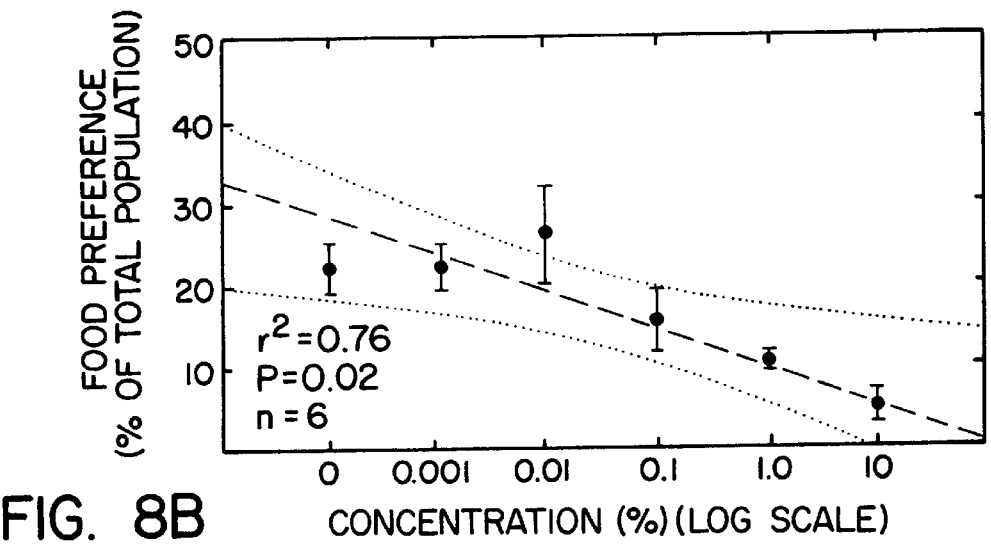
FIG. 8B shows the results of granary weevil and wheat kernels treated with pea protein.
Figure 8C:
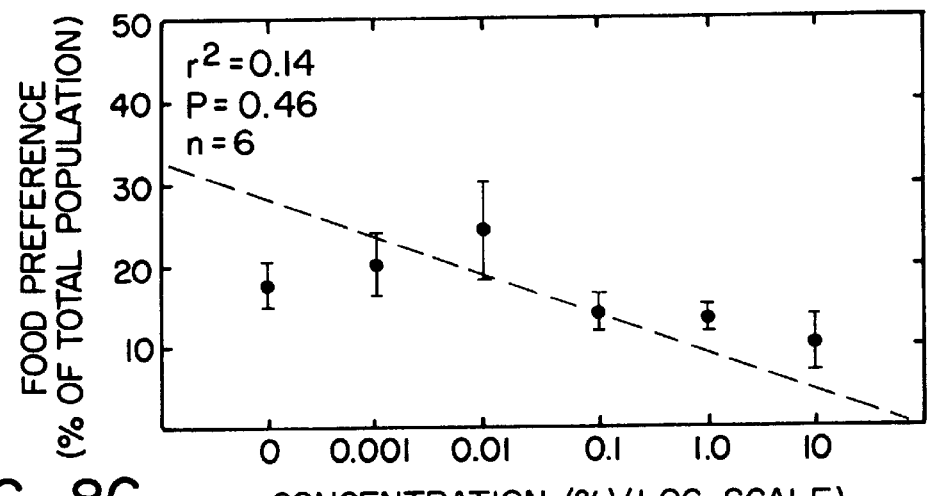
FIG. 8C shows the results of rusty grain beetle and wheat kernels treated with pea fiber. Adults were held on pea protein or pea fibre (0.01%) for 4 weeks before conducting multiple choice tests of corresponding pea extract. Dashed lines represents insects never exposed to pea extracts (data from FIGS. 4, 5).

After 4 weeks feeding on pea protein treated wheat (0.01%), rusty grain beetle and rice weevil were still repelled by pea protein-rich or pea fibre-rich fractions (FIGS. 8A, B). The responses were the same as insects never exposed to pea extracts (FIGS. 4A, B). In contrast, rusty grain beetle adults lost sensitivity to the repellent action of pea fibre after feeding on fibre-treated wheat (0.01%) for 4 weeks (FIG. 5C), although insects never exposed to pea fibre were repelled (FIG. 5A).

Example 3

Protection of Barley Flour or Barley Protein from Insects

Barley flour, barley protein, pea protein and their mixtures, which are used in famine relief programs, were tested to determine if they are protected from insects.

Red flour beetle adults, 1 to 2 weeks old, were placed in 20 g of food. There were 8 treatments: wheat flour, pea flour (whole ground peas), barley protein, barley flour, and 50:50 mixes of barley flour and pea protein, wheat flour and pea protein, wheat flour and pea flour, as well as barley flour and pea flour. There were 5 replicates with 10 insects (not sexed) per vial. After 2 weeks at 30° C., 70% RH, the adults were removed the number of dead counted and the larvae and eggs left for an additional 5 weeks to determine the number of offspring.

After 2 weeks, insects held on the pea flour had the highest mortality, with the other foods causing little mortality. The offspring were greatly reduced in all but the 100% barley treatment and the wheat flour and pea flour mixture (Table 9).

Thus, mixtures of barley flour with pea protein or pea flour would greatly reduce infestations by the red flour beetle. The other insects that commonly feed on flour are more sensitive to the pea extracts (Table 3) and should therefore not be able to infest the barley pea flour mixture.

TABLE 9

Insecticidal activity of cereal materials on the red flour beetle.

| Treatment | Concentration (%) | Mortality (%) at week 2 | No. of offspring (Mean ± SD) |
|---|---|---|---|
| Wheat Flour (WF) | 100 | 0 | 157 ± 19 |
| Pea Flour (PF) | 100 | 22 | 0 |
| Barley Protein (BP) | 100 | 2 | 69 ± 7 |
| Barley Flour (BF) | 100 | 0 | 41 ± 5 |
| BF + PP[1] | 50/50 | 2 | 3 ± 1 |
| WF + PP | 50/50 | 6 | 1 ± 1 |
| WP + PF | 50/50 | 0 | 27 ± 7 |
| BF + PF | 50/50 | 0 | 3 ± 3 |

[1]PP = Pea Protein

Example 4

Liquid Applications of the Protein-Rich Pea Fraction

The efficacy of the pea protein-rich fraction when applied to wheat kernels in a liquid form, was determined.

One hundred g of pea protein-rich fraction was dissolved in 900 ml of double distilled $H_2O$ (concentration: 10%, wt:wt) in a 4 L flask and stirred for 24 h at 2.5° C. The extract was centrifuged at 7500 g for 50 min at 4° C. The supernatant, the water soluble fraction, was applied to wheat kernel by a small atomizer at concentrations of 0, 1, 2, 4, 6, and 8% (wt:wt). Since only 40% parent material dissolved into the liquid, these concentrations are the equivalent of 0, 0.04, 0.08, 0.16, 0.24, and 0.32% parent pea protein-rich fraction. After mixing, wheat kernels were placed in a glass jar and rotated on a barrel roller for 30 min to obtain a uniform treatment. Treated wheat was kept at room temperature over night (or longer) to reduce wheat moisture to about 15%. Ten adult rice weevils were introduced to each vial, 5 vials/treatment and 20 g of wheat/vial. After one week at 30° C. and 70% R.H., mortality of adult beetles was determined.

Figure 9:
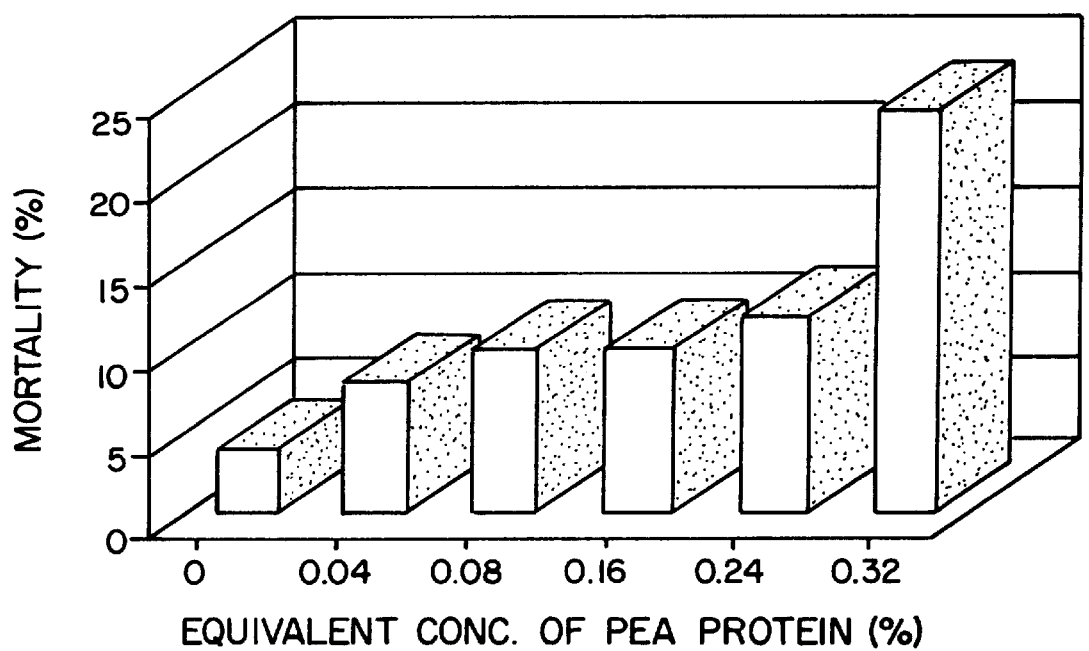
FIG. 9 shows the effect of a liquid application of a pea protein-rich fraction on the mortality of rice weevil after one week.

Clearly, pea protein-rich faction possessed insecticidal activity when applied in a liquid form (FIG. 9) and caused 24% mortality at 8% (0.32% equivalent of parent material) (FIG. 9). Liquid formulations are easier to apply than powders and they cause fewer visible residues. In order to maintain effective concentrations of the liquid extract a more concentrated liquid form could be used as a way of increasing its efficacy.

Example 5

Survey of Different Pea Varieties for their Insecticidal Activities

Different pea varieties were screened for their insecticidal activities. Thirty one commercial pea varieties and 33 wild peas (mostly *Pisum satvium* with a few *Pisum fulvium*) were screened.

With commercial varieties approximately 150 g seed were milled with a Stein mill for 3 min. With wild peas, 5–60 g seed (based on available seed) were milled for 5 min. A preliminary test was conducted with one field pea to determine what dosage should be used for the large scale screening. Eight concentrations (0–2%) were used in this study. Whole pea flour was mixed with wheat, and shaken for 2 min to obtain a uniform distribution. The bioassay was conducted as described above (Example 1). After two weeks, the adults were shaken off and mortality was determined.

Based on the result from the preliminary test, a 0.3% concentration was used for screening all varieties. One hundred g of wheat kernels were treated with 0.3 g pea powder. After mixing and shaking, treated wheat was filled in 5 vials (5 replicates). The bioassay was performed as mentioned above (Example 1). After two weeks, mortality was determined, adult beetles were removed, and the rest was kept in the incubator for another 5 weeks before counting the offspring as adults.

Figure 10:
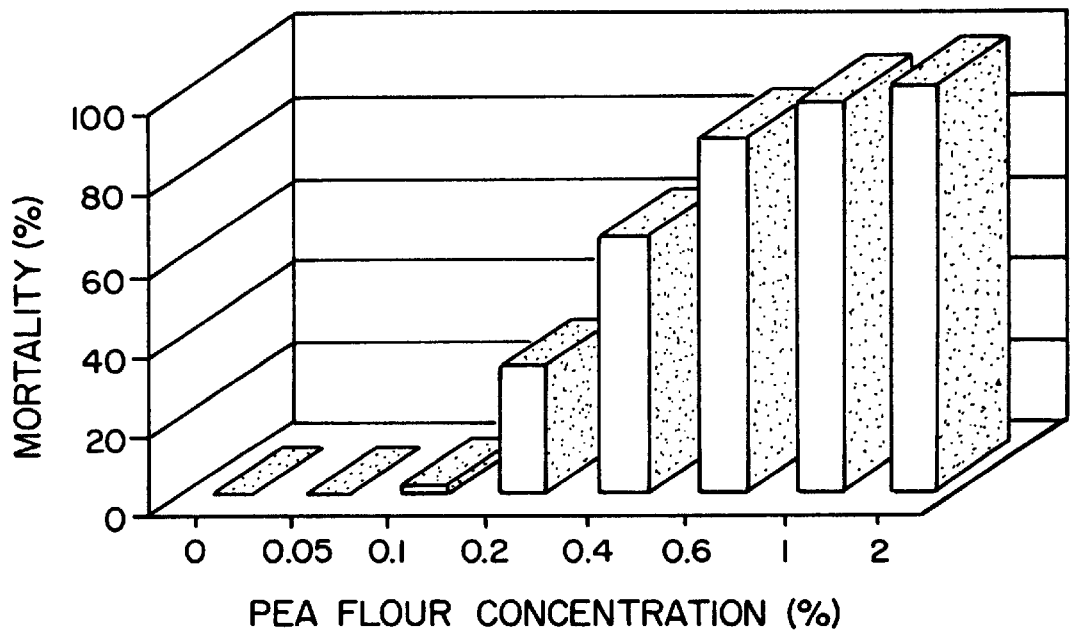
FIG. 10 shows the preliminary bioassay (2 week duration) of whole pea flour against rice weevil.

For the rice weevil, the whole pea flour 50% mortality was obtained at approximately 0.3% after 2 weeks (FIG. 10), this concentration is about ten fold greater than pea protein ($LC_{50}$=0.02%, Example 1).

For the 31 commercial varieties, the 2 week mortality ranged from a high of 92% with Celeste to a low of 32% with Impala. The offspring were reduced to a low of 25% to a high of 80% of the control offspring (Table 10). For the 33 wild peas, the 2 week mortality ranged from 100% to 6% and the offspring were reduced from 25% to only 95% of the control offspring (Table 11).

TABLE 10

Insecticidal activity of commercial pea varieties against the rice weevil. Parent mortality was assessed after 2 weeks, the number of offspring was assessed after 5 weeks.

| Variety | Parent Mortality (%) | Offspring Number | Offspring as Percent of Control |
|---|---|---|---|
| Celeste | 92 | 56 | 25 |
| Tamor | 90 | 70 | 21 |
| Tipu | 86 | 99 | 44 |
| CSP-5 | 84 | 74 | 33 |
| Trapper | 84 | 120 | 53 |
| Titan | 84 | 91 | 41 |
| Trump | 82 | 113 | 50 |
| Princess | 80 | 103 | 46 |
| Richmond | 78 | 112 | 50 |
| Century | 76 | 90 | 40 |
| Patriot | 76 | 89 | 40 |
| Bohatyr | 74 | 56 | 25 |
| Victoria | 74 | 103 | 46 |
| ORB | 72 | 96 | 43 |
| Radley | 70 | 109 | 48 |
| Stehgolt | 70 | 144 | 64 |
| Carneval | 68 | 103 | 46 |
| Yellowhead | 66 | 151 | 67 |
| Spring | 64 | 131 | 58 |
| Highlight | 64 | 88 | 39 |
| Express | 64 | 92 | 41 |
| Tara | 62 | 130 | 58 |
| Danto | 62 | 113 | 50 |
| Topper | 60 | 117 | 52 |
| Montana | 58 | 127 | 56 |
| Baroness | 56 | 123 | 55 |
| Miko | 56 | 130 | 58 |
| Fluo | 54 | 156 | 69 |
| Emerald | 42 | 172 | 76 |
| Sirius | 40 | 178 | 79 |
| Impala | 32 | 180 | 80 |
| Control | 0 | 226 | — |

TABLE 11

Insecticidal activity of wild pea varieties against the rice weevil. Parent mortality was assessed after 2 weeks, the number of offspring was assessed after 5 weeks.

| Variety | Parent Mortality (%) | Offspring Number | Offspring as Percent of Control |
|---|---|---|---|
| 512072 | 100 | 55 | 25 |
| 358612 | 98 | 65 | 29 |
| 505059 | 96 | 76 | 34 |
| 344003 | 92 | 79 | 35 |
| 273029 | 90 | 71 | 32 |
| 358611 | 90 | 75 | 33 |
| 358613 | 88 | 79 | 35 |
| 512074 | 88 | 81 | 36 |
| 512073 | 88 | 84 | 37 |
| 358615 | 86 | 70 | 31 |
| 512066 | 86 | 110 | 49 |
| 560056 | 84 | 79 | 35 |
| 358610 | 82 | 82 | 36 |
| 512059 | 82 | 106 | 47 |
| 512075 | 82 | 79 | 35 |
| 358617 | 80 | 90 | 40 |
| 358618 | 80 | 112 | 50 |
| 358616 | 74 | 98 | 44 |
| 344012 | 74 | 82 | 36 |
| 358608 | 70 | 101 | 45 |
| 344005 | 66 | 113 | 50 |
| 560057 | 52 | 151 | 67 |
| 512077 | 50 | 145 | 64 |
| 343993 | 48 | 193 | 64 |
| 343991 | 44 | 171 | 76 |
| 269760 | 40 | 160 | 71 |
| 344011 | 34 | 155 | 69 |
| 343998 | 32 | 170 | 76 |
| 560065 | 18 | 183 | 81 |
| 560066 | 12 | 203 | 90 |
| 560064 | 10 | 214 | 95 |
| 560072 | 6 | 202 | 90 |
| 343976 | 6 | 153 | 68 |
| Control | 0 | 226 | — |

There exists considerable variation in the insecticidal activity of the commercial pea varieties. As these varieties were all grown in the same growing season from the same field these differences are unlikely to be due agronomic factors. There are small variations in the amount of protein in commercial peas, from 22 to 25%, so the amounts of protein are unlikely to cause this wide variation. Not wishing to be bound by theory, this variation may arise from differences in the type of protein in the seeds, or other components, such as fibre, that are responsible for this variation.

Example 6

Efficacy of Heated Protein-Rich Pea Fraction

In order to characterize the active ingredient in the pea protein-rich fraction, this fraction was heated. If the active ingredient is a protein or a protein-like substance heat treatment should denature the protein and reduce the activity. In this Example it was also determined if the temperature generated by the grinding process affect the bioactivity.

One hundred ml of pea protein supernatant (as prepared in Example 4) was heated to 100° C. for 30 min. The heated supernatant was then freeze dried. Another 100 ml non-heated supernatant was also freeze-dried as a control. The freeze-dried powders were ground using a mortar and pestle and mixed with wheat at a concentration of 0.5%. After mixing, treated wheat was shaken for 2 min to obtain a uniform distribution. Untreated wheat and pea protein-rich faction (parent material) were used as controls. The bioassay was conducted as described in Example 5. Mortality was determined after one week.

One hundred and fifty g of seed of a field pea were milled with a Stein mill for 3 or 5 min. at room temperature or −40°

C., which generated temperatures from 18 to 70° C. in the pea flour. Pea flour was mixed with wheat at concentrations from 0 (control) to 1%, 6 concentrations were used for each type of flour, and shaken for 2 min. The bioassay was conducted as in Example 5 above. Mortality was determined after one week.

Figure 11:
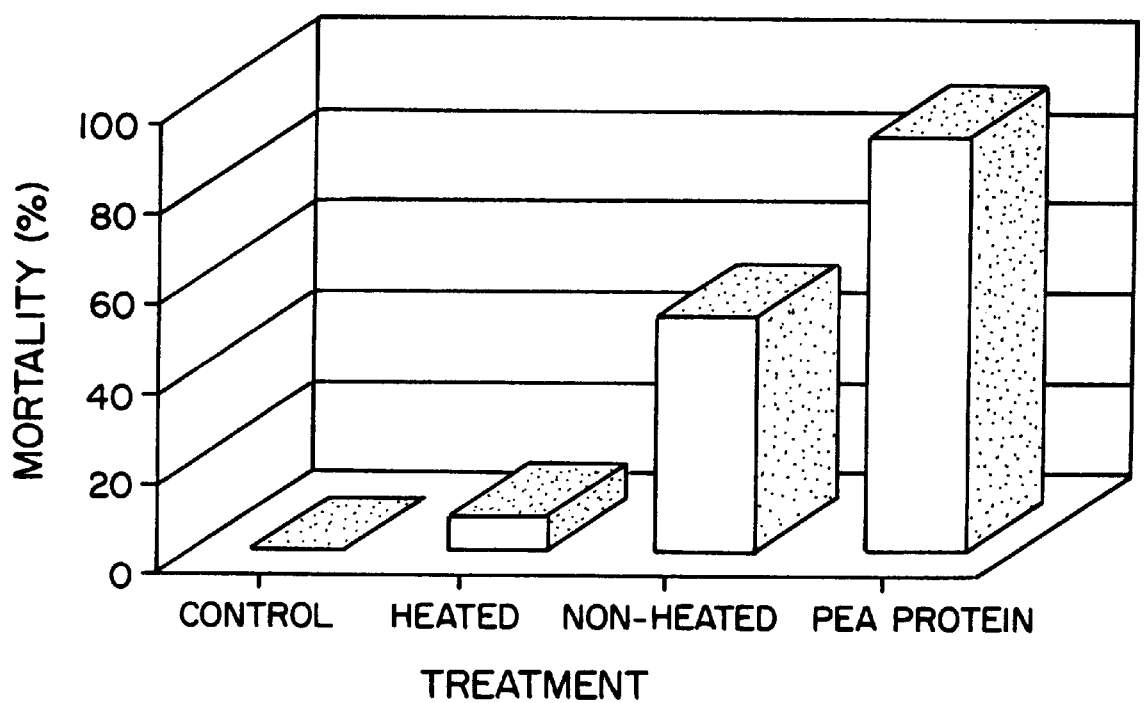
FIG. 11 shows the effect of heating and water extraction on the toxicity of pea protein to rice weevil after one week.

Heating the pea protein-rich fraction greatly reduced the insecticidal activity of the pea extract. The non-heated, freeze dried supernatant had lower activity than the parent pea protein (FIG. 11).

There were no significant differences in insecticidal activity of pea flour exposed to various temperatures (from 18 to 70° C.) when pea seed was ground (Table 12). It should be noted that pea flour was exposed to various temperatures for only short periods of time, and these results do not implicate that heating in pea mill processing would not reduce bioactivity.

TABLE 12

Effect of temperature associated with grinding of pea seed (150 g) on its insecticidal activity.

| Environmental Temperature (° C.) | Grinding time (min.) | Temperature in pea flour | $LC_{50}$ (95% conf. interval) (%) |
|---|---|---|---|
| −40 | 3 | 18 | 0.55 (0.36–0.84) |
| 20 | 3 | 60 | 0.35 (0.24–0.52) |
| −40 | 5 | 28 | 0.4 (0.33–0.60) |
| 20 | 5 | 70 | 0.45 (0.28–0.54) |

The active fraction is thus heat unstable, this suggests that it is protein in nature but is not an absolute proof. Inactivation when exposed to protease enzymes would be a more definite proof. Heating as a powder during grinding in the pea varieties did not reduce activity. Heating while in solution may be more detrimental than heating when dry.

Example 7

Fractionation of the Pea Protein-Rich Fraction

Figure 12:
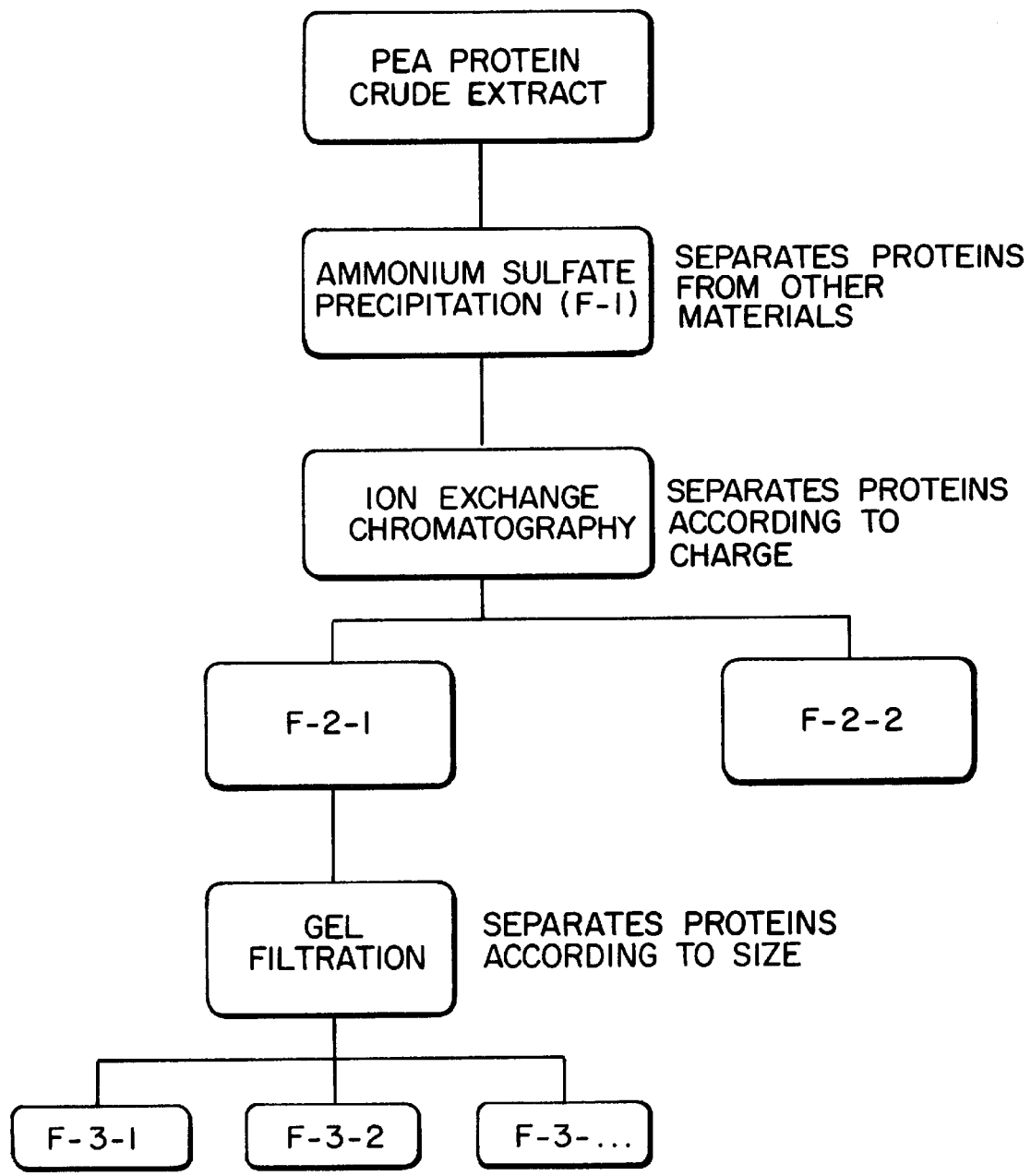
FIG. 12 illustrates the purification method used for the isolation of the active ingredient from the pea protein-rich fraction.

In this example the separation and partial purification of the active constituent in the protein-rich fraction is described. The techniques used for isolation of the active components are: separation by precipitation (ammonium sulfate precipitation), separation by adsorption (ion exchange chromatography), and separation in solution (gel filtration). The purification method is depicted in FIG. 12. Details are provided below.

Two hundred g of pea protein-rich fraction was dissolved in 1800 ml of double distilled $H_2O$ or 50 mM phosphate buffer (concentration: 10%, wt:wt) in a 4 L flask and stirred for 24 h at 2.5° C. The extract was centrifuged at 10,000 g for 30 min at 4° C. The supernatant was then adjusted to different saturation rate (Table 13) with ammonium sulphate at room temperature (25° C.) to precipitate protein. After 30 min, it was centrifuged at 10,000 g for 30 min at 4° C. The pellet was resuspended with half volume of double distilled water, dialysed against prechilled distilled water (6×5 L) for 48 hrs at 2.5° C., and then, followed by centrifugation at 5,000 g for 10 min at 4° C. The supernatant was frozen and freeze-dried. These initial protein fractions were called F-0-x (x=1–12) (Table 13).

Insect bioassay with these fractions indicated that: extractions with buffer and double distilled water had similar activity and fractions between 30% to 100% saturation with ammonium sulfate had similar activity (Table 13). Also, since 0–30% saturation with ammonium sulfate only recover a small portion of precipitated protein (Table 13), 90% saturation with ammonium sulfate was used for protein precipitation, and this fraction was called F-1. The F-1 fraction was further purified by ion-exchange chromatography (DEAE Sephadex A-25).

Five g of F-1 was dissolved in 200 ml Tris-HCl buffer (50 mM, pH 8.0; starting buffer), and applied into the ion-exchange column. The non-absorbed material (pass-through filtrate) was eluted and collected (F-2-1). The bounded material was eluted stepwise in the presence of 0.5 M NaCl (F-2-2) and 2 M NaCl (F-2-3) in the starting buffer. All three fractions were frozen and freeze-dried. The dry materials were resuspended with appropriate amount of double distilled water, dialysed against prechilled distilled water (6 changes of 5 L) for 48 hrs at 2.5° C. and freeze-dried.

The active fraction from ion-exchange chromatography, which was eluted using the starting buffer (0M NaCl), was further purified by gel filtration using Sephadex G-100. One half of g of F-2-1 was dissolved in 2 ml Tris-HCl buffer, and injected into the column. The material was eluted by pumping starting buffer at a flow rate of 0.2 ml/min, and fractions collected every 60 min. The protein content of the fractions was determined by the Bradford method (1976) using bovine serum albumin as a standard.

One hundred g of wheat kernels were treated with different fractions at 0.3% (wt:wt) for F-0-x fractions, and 0.2% for all other fractions. After mixing and hand-shaking for 2 min., 20 g of treated wheat was filled in a glass vial (5 replicates). Ten adult S. oryzae were introduced to each vial. After one week at 30° C. and 70% R H., mortality was determined.

One-week mortality of the rice weevil held on wheat kernels treated with parent pea protein (P.P.P.) and different precipitated-protein fractions are shown in Table 13. All fractions at >30% saturation caused similar mortality.

TABLE 13

One-week mortality of the rice weevil on wheat treated with different ammonium sulfate precipitation fractions (concentration = 0.3%, wt:wt)

| Fraction | Extraction medium | Saturation rate (%) | Recovery (%) | Mortality (%) |
|---|---|---|---|---|
| F-0-1 | Buffer | 0–30 | 12.6 | 50 |
| F-0-2 | Buffer | 30–40 | 29.6 | 92 |
| F-0-3 | Buffer | 40–50 | 28.5 | 90 |
| F-0-4 | Buffer | 50–60 | 18.9 | 96 |
| F-0-5 | Buffer | 60–100 | 10.4 | 100 |
| F-0-6 | Buffer | 0–35 | 34.8 | 92 |
| F-0-7 | Buffer | 35–45 | 28.5 | 98 |
| F-0-8 | Buffer | 45–55 | 23.9 | 98 |
| F-0-9 | Buffer | 55–100 | 12.8 | 96 |
| F-0-10 | Water | 0–30 | 3.7 | 65 |
| F-0-11 | Water | 30–60 | 67.6 | 96 |
| F-0-12 | Water | 6–100 | 28.7 | 96 |
| P.P.P* | | | | 82 |
| Control | | | | 0 |

*Parent pea protein.

Figure 13:
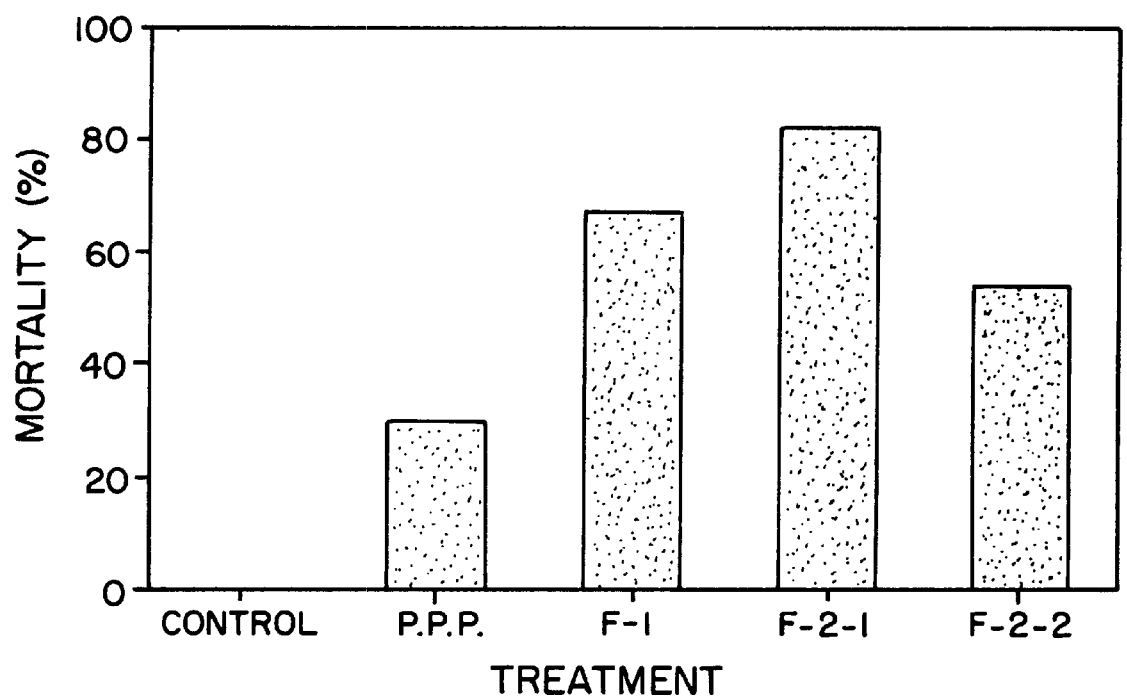
FIG. 13 shows the one-week mortality of rice weevil held on wheat kernels treated with parent pea protein (P.P.P.), an ammonium sulfate precipitation fraction (F-1), and two ion exchange chromatography fractions (F-2-1 and F-2-2) (concentration=0.2%, wt:wt).

FIG. 13 shows mortality of the rice weevil caused by other fractions. The parent pea protein-rich fraction caused 30% mortality. However, a significant higher mortality was obtained by the treatments with amnmonium sulfate precipitation fraction (90% saturation) (F-1, mortality=67%) and ion-exchange fraction (F-2-1, mortality=82%). The parent pea protein-rich fraction is only 60% protein and this may account for its lower activity.

Figure 14:
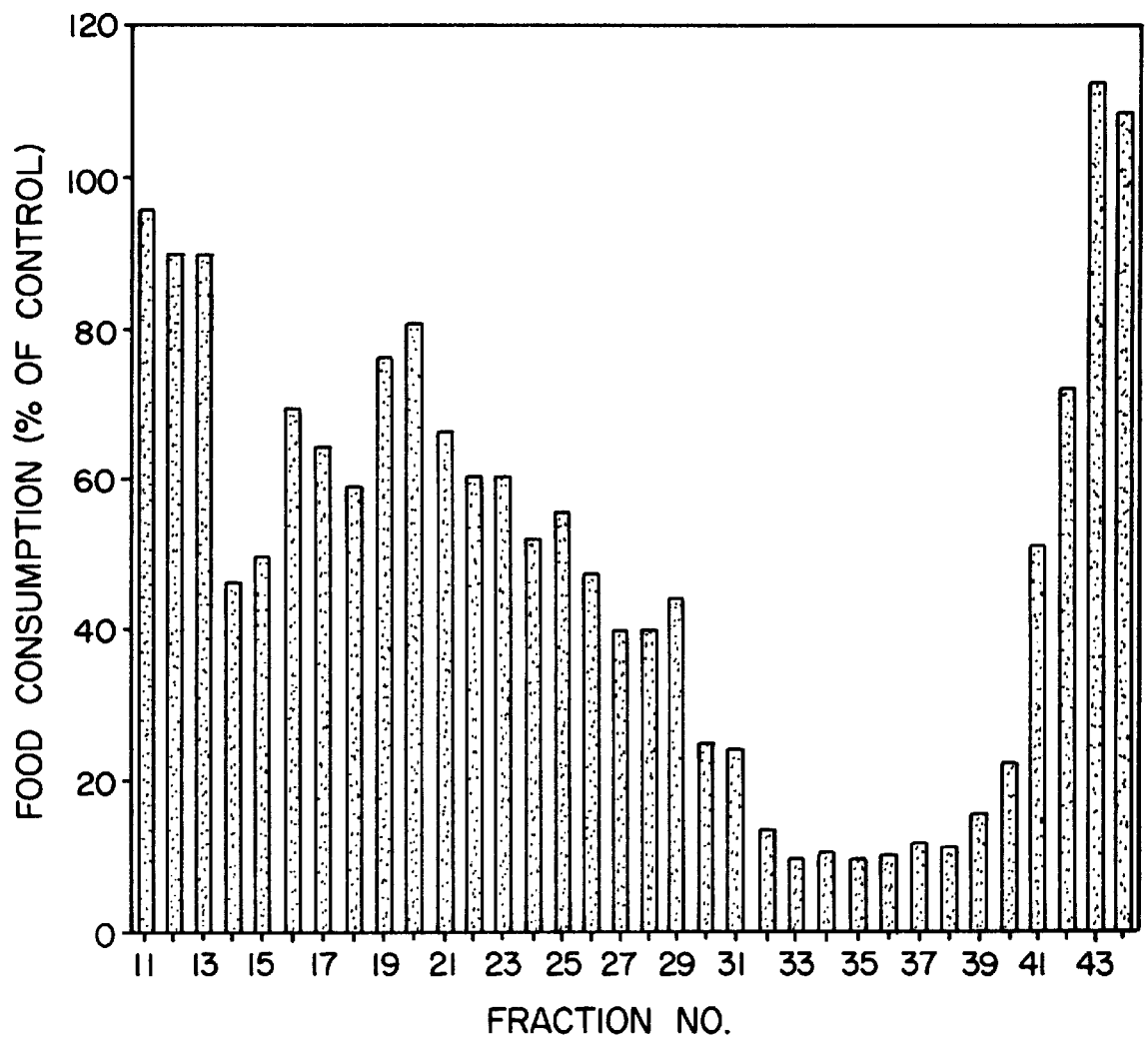
FIG. 14 shows the food consumption (% of control) of rice weevil fed on flour disk treated with gel filtration (G-100) fractions.

Food consumption (% of control) of the rice weevil on flour disk treated with G-100 fractions are shown in FIG. 14.

It clearly demonstrated that fractions of #32–39 were very active compared with others, food consumption was less than 20% of control. Fractions 32–39 corresponded to the "salt" volume of the column and contained low molecular weight substances outside the lower globular protein fractionation range (<4000) of Sephadex G-100 (Pharmacia, 1995). Continuous ultraviolet monitoring at 280 nm of the column effluent during the collection of fractions 32–39 revealed no peaks. The absorbance at 280 nm of each one of the fractions 32–39 measured in quartz cuvetts in a spectrophotometer was zero. The protein content of fractions 32–29 was determined by the Bio-Rad Protein Assay was zero.

Example 8

Bioactivity of Protease Treated Fractions

To test if protein and/or polypeptides are responsible for the observed insecticidal activity, a non-specific protease (bromelian) was used to react with the active fraction. If protein and/or polypeptides are involved in the insecticidal activity, this non-specific enzyme should cleave protein and/or polypeptides and abolish the activity. The protease was dissolved in a 10 mM potassium phosphate buffer with 10 mM KCI (pH=6.0) at concentrations of 3, 6, 12, 25, 50, 100, 200 and 400 $\mu$g per 0.9 ml buffer solution. G-100 fractions (0.1 ml), or water (0.1 ml), were mixed with 0.9 ml enzyme solutions and incubated for 30 min at 37° C. After 30 min, the reaction was stopped by placing at 0° C. One ml solution was mixed with 200 mg wheat flour to prepare flour disks for bioassay.

The rice weevil [*Sitophilus oryzae* (L.)] was used for all bioassays. One ml of an aqueous solution containing test material was mixed with 200 mg wheat flour. Distilled water was used as a control. Approximately 100 $\mu$l of the stirred suspension were removed and placed in the bottom of a polystyrene Petri dish, and allowed to air dry overnight at room temperature to produce the flour disks. The disks were equilibrated at 30±1° C. and 70±5% r.h. for 24 hr to stabilize the moisture content. Individual weighed disks and 5 adult beetles (1 to 7 days old, starved for 24 hrs before use) were transferred to petri dishes and kept at 30±1° C. and 70±5% r.h. for 4 days (5 replicates) before the remains of the flour disk were weighed. For materials from different pea varieties, five concentrations were prepared for each test material and the $EC_{50}$ value (effective concentration resulting 50% reduction of insect food consumption relative to controls) was calculated.

Figure 15:
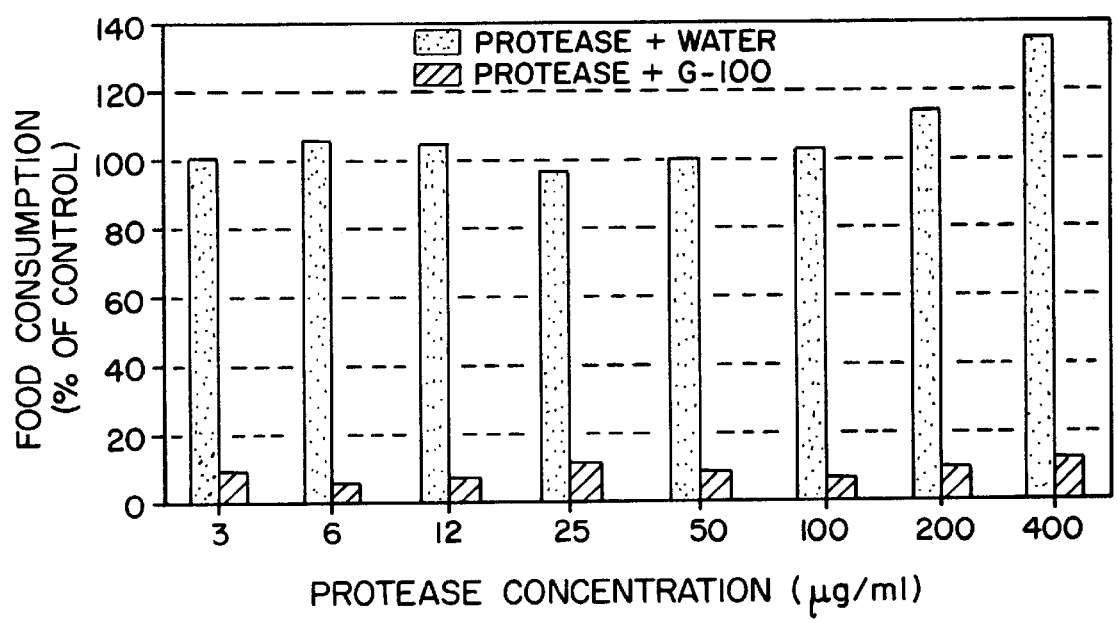
FIG. 15 shows the food consumption (% of control) of rice weevil fed on flour disks treated with G-100 fraction with and without protease.

Incubation of fractions 31–39 obtained from after G-100 gel filtration (Example 7, and FIG. 14) with the non-specific protease bromelain did not reduce the activity of any of the fractions (FIG. 15). These observations taken together show that the active component from peas is protease insensitive.

Example 9

Bioactivity of Saponin Extracts From Peas

Saponins, characterized by their bitter taste, foaming in aqueous solutions and haemolytic activity, are a diverse group of secondary plant metabolites containing a carbohydrate moiety (mono- or oligosaccharide) attached to either a steroid ($C_{27}$) or a triterpenoid ($C_{30}$). Saponins are reported to have insecticidal activity. Saponin extractions were prepared from the seeds of commercial peas (*Pisum sativum*). Approximately 100 g seeds were milled with a Stein mill for 5 minutes and 10 g flour was extracted with 1000 ml chloroform for 16 hrs in a Soxhlet extractor to remove pigments and lipids. Three hundred mg air-dried defatted flour was refluxed for 5 min with 60 ml 80% MeOH, then transferred to a centrifuge tube with 2×5 ml 80% MeOH rinse. The slurry extracts were centrifuged at 10,000 rpm for 10 min. The pellet was dried at room temperature for testing the residual insecticidal activities and the supernatant was evaporated to 7–8 ml under reduced pressure in a rotary evaporator at 37° C. The solution and additional 3 ml distilled water rinse were applied to a reverse phase $C_{18}$ cartridge (Sep Pak, $C_{18}$). The column was washed with 3×5 ml 30% MeOH then eluted with 4×5 ml MeOH. The MeOH elute was evaporated to dryness in a rotary evaporator, and then dissolved in 6 ml distilled water (at a concentration equivalent to 50 mg defatted flour per ml). This extract was used for bioassay.

HPLC analysis of saponin was determined by an isocratic solvent system (methanol-2-propanol-water-acetic acid, 70.0:6.0:23.9:0.1, v/v) on a standard $C_{18}$ reverse phase column (5 $\mu$m ODS) using a Solvent Delivery Module (SPE Limited, Model 5700) with a UV detector (Pharmacia LKB VWM 2141). Soyasaponin I from soybean was used as a standard on HPLC analysis (Soyasaponin I was kindly provided by Drs. Kazuyoshi Okubo and Yumiko Yoshiki, Department of Applied Biological Chemistry, Tohoku University, Aobako, Sendai, Japan).

One ml saponin extract (50 mg equivalent/ml) was loaded on ion exchange columns (2 ml volume) with Dowex AG-SOW [H$^+$] and Dowex AG-1 [Cl$^-$] respectively. The columns were eluted with 10 ml distilled water. The water elute was evaporated to dryness in a rotary evaporator, and then dissolve in 1 ml distilled water. The water fractions were used for HPLC analysis and bioassay.

Haemolytic activity (capacity to break-up red blood cells) of saponin extracts from pea was determined by a modified procedure of Rycroft et al. (1991, J. Gen. Microbiol. 137, 561–568)). Fresh citrated sheep blood was centrifuged at 2000 rpm for 30 min and the supernatant removed. The remaining erythrocytes were resuspended with 50 mM Tris-HCI, 150 mM NaCl (pH 7.4) buffer and washed three times by centrifugation. A 2.5% suspension of erythrocytes was prepared using the same buffer. A serial dilution of standard saponin from saponaria species was prepared to generate a standard curve. One ml erythrocyte suspension and 0.5 ml saponin solution were gently mixed in a micro centrifuge tube and incubated at 37° C. for 60 min. After incubation, the mixture was centrifuged for 20 second in a micro centrifuge and the $A_{541}$ was measured by a spectrophotometer. Haemolytic activity of the pea extracts was determined by comparing to the standard curve and expressed as mg saponin equivalent per g pea flour.

Cholesterol reacts with saponins (forms complexes) and negates the saponin toxicity (Ishaaya et al. 1969, J. Sci. Food Agric. 20, 433–436; Shany et al. 1970, J. Sci. Food Agric. 21, 508–510). In this study, the possibilities of abolishing the deleterious effects of saponins by cholesterol were investigated. Four mg cholesterol in 100 $\mu$l hot ethanol was added to various concentrations of pea extract (5–20 mg equivalent in 0.9 ml distilled water) and standard saponin from saponaria species (0.2–1.0 mg in 0.9 ml distilled water), and mixed with 200 mg wheat flour for bioassay. Cholesterol solution (4 mg) was used as a control. The same concentrations of pea extract and standard saponin were also prepared for bioassay.

The bioassays were as described in the preceding example. Standard soyasaponin 1 (0.125–2.0 mg/ml solution) was used as a standard.

Based on a literature search and our observations, we initially assumed that saponin played a major role on the observed insecticidal activity. However, further investigations indicated that saponins in the pea extracts were not responsible for the observed insecticidal activity. This conclusion was proved by the following data.

(1) Soyasaponin I was not active against the test stored-product insect.

Bioassay with pure chemical soyasaponin I indicated that, neither at its natural concentration present in peas (~0.6 mg/g) nor at a concentration as high as 10 mg/g, soyasaponin I was not active against the test insect (Table 14).

TABLE 14

Insecticidal activity of Soyasaponin I on the rice weevil, *S. oryzae*

| Concentration (mg/g) | Food consumption (mg/day/insect) | % of control |
|---|---|---|
| 0.00 | 0.52 a* | 100 a |
| 0.63 | 0.52 a | 99.8 a |
| 1.25 | 0.44 a | 84.2 a |
| 2.50 | 0.43 a | 82.8 a |
| 5.00 | 0.46 a | 88.4 a |
| 10.0 | 0.51 a | 97.9 a |

*Means followed by the same letters indicate no significant different in the LSD test.

(2) No significant correlation was found between soyasaponin I content in different pea varieties and their insecticidal activity.

Insecticidal activity of different pea flour and saponin extracts, and soyasaponin content in different peas are shown in Table 15. Using the newly developed flour disk bioassay, different pea varieties also showed great differences in their insecticidal activities, consistent with and significantly correlated to our previous observation using classical bioassay method ($r^2=0.59$, P=0.0008, n=15). Significant correlation for activities between unfractionated flour and extract fraction ($r^2=0.86$, P=0.0001, n=15), indicated that the active component responsible for the observed activity was extracted by our extraction procedures. However, no significant correlation was found between soyasaponin I content in different pea varieties and their insecticidal activity ($r^2=0.09$, P=0.2824, n=15), suggested that the observed activity in the extractions could not be explained by soyasaponin I.

(3) No significant correlation was found between haemolytic activity of pea extracts and their insecticidal activity.

Haemolysis is considered as one of the important characteristics of saponins, and haemolysin bioassay has been used as a common procedure to demonstrate the presence of saponin in different legumes (Khalil et al. 1994, Food Chem. 50, 197–201). Our haemolysin study clearly indicated that saponins were present in our pea extracts (Table 15). However, no significant correlation was found between haemolytic activity of pea extracts and their insecticidal activity ($r^2=0.02$, P=0.6282, n=15), indirectly suggesting that saponins were not responsible for the observed insecticidal activity of pea extracts.

(4) Ion exchange chromatography separated soyasaponin I from active fraction.

The water eluent from an ion exchange column (Dowex AG-1 [Cl$^-$]) showed insecticidal activity but no saponin was detectable; in contrast, the water eluent from cation exchange column (Dowex AG-50W [H$^+$]) showed no insecticidal activity but considerable amounts of saponin (Table 16).

TABLE 16

Insecticidal activity and soyasaponin I content of fractions from ion exchange columns

| | Insecticidal activity | | |
|---|---|---|---|
| Fraction | Consumption (mg/day/insect) | % of control | Soyasaponin I (mg/g flour) |
| Control | 0.48 | 100 | 0 |
| Dowex AG-1 | 0.08 | 16 | ND* |
| Dowex AG-50W | 0.47 | 98 | 0.2 |

*Not detected.

(5) Cholesterol did not overcome toxicity of pea extract on the test insect.

Figure 16A:
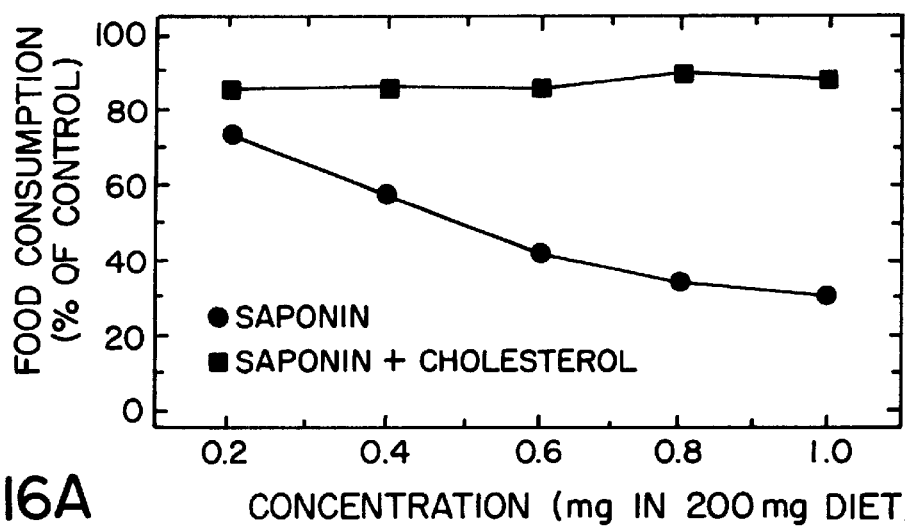
FIG. 16 shows the effect of saponin (FIG. 16A), pea extract (FIG. 16B) and pea flour (FIG. 16C) on rice weevil and their detoxification by cholesterol.
Figure 16B:
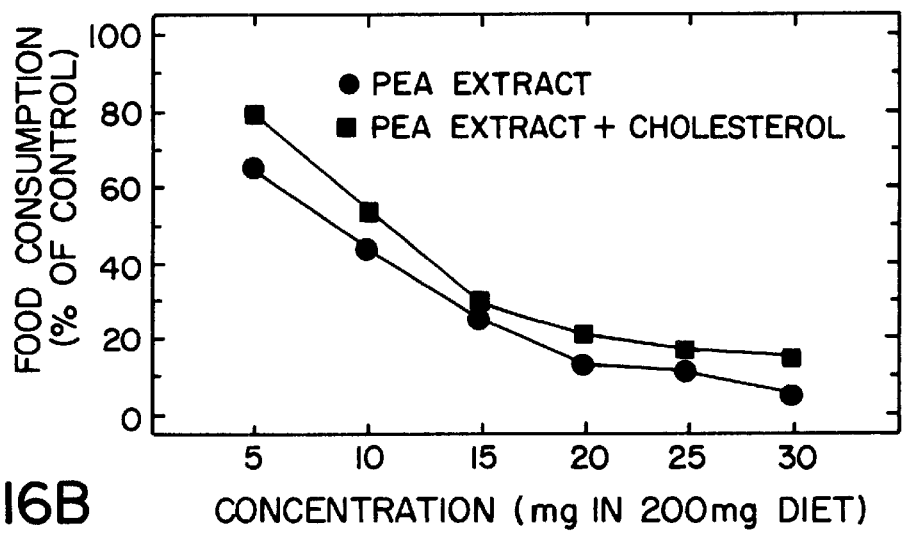
Figure 16C:
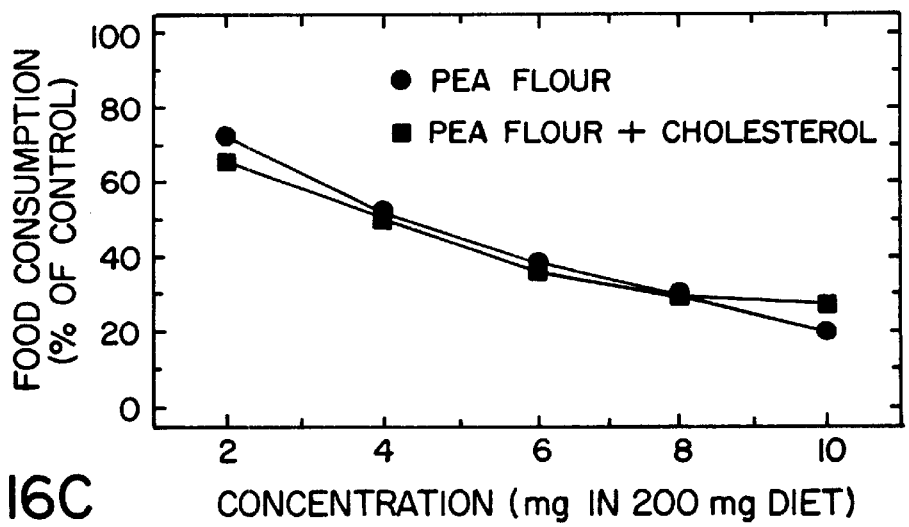

Our study was demonstrated that saponin from saponaria species was toxic to insect and cholesterol could detoxificate the saponin (FIG. 16, A). However, toxicity of pea extract or flour could not be abolished by cholesterol (FIGS. 16, B and C), suggesting that the active component in pea was not a saponin.

TABLE 15

Insecticidal, haemolytic activity and soyasaponin I content of pea varieties

| | Mortality (%) | EC$_{50}$* (mg equivalent/g diet) | | | Haemolysis |
|---|---|---|---|---|---|
| Pea variety | (Classical method) | Unfractionated flour | Extract fraction | Soyasaponin (mg/g flour) | (mg saponin eqiv/g flour) |
| CSP-5 | 84 | 13.5 | 17.5 | 0.49 | 3.65 |
| Titan | 84 | 14.0 | 27.5 | 0.59 | 3.70 |
| Tamor | 90 | 14.5 | 28.5 | 0.45 | 3.47 |
| Express | 64 | 14.5 | 25.5 | 0.55 | 3.52 |
| Trapper | 84 | 14.5 | 35.0 | 0.42 | 3.76 |
| Tipu | 86 | 15.0 | 35.0 | 0.79 | 4.01 |
| Trump | 82 | 16.0 | 39.0 | 0.66 | 3.38 |
| Patriot | 76 | 16.0 | 39.0 | 0.55 | 3.62 |
| Bohatyr | 74 | 17.5 | 49.5 | 0.55 | 3.66 |
| Emerald | 42 | 18.0 | 41.0 | 0.58 | 3.92 |
| Celeste | 92 | 20.0 | 49.5 | 0.46 | 3.94 |
| Miko | 56 | 20.0 | 43.5 | 0.62 | 3.51 |
| Fluo | 54 | 21.0 | 59.5 | 0.57 | 3.32 |
| Impala | 32 | 26.5 | 61.5 | 0.56 | 3.68 |
| Sirius | 40 | 28.0 | 96.0 | 0.38 | 3.55 |

*Effective concentration resulting 50% reduction of insect food consumption relative to controls.

Example 10

Solvent Extraction of Pea Protein-Rich Fraction

In order to obtain an efficient extraction method and further characterize the insecticidal fractions from the protein-rich fractions of pea, a solvent extraction method was examined.

Defatting the Air-Classified Protein-Rich Pea Fraction

One hundred and twenty grams of air-classified protein-rich pea flour obtained as in Example 1 were stirred in one liter of chloroform for one hour. The mixture was filtered in a Buchner funnel and the cake washed with 100 ml chloroform and then air dried.

Solvent Extraction of the Defatted Protein-Rich Pea Fraction

Samples (300 mg) of the defatted protein-rich pea fraction were extracted under various conditions to determine an efficient method for extracting insecticidal activity. Samples were homogenized for 1 min in 70 ml of each of the solvents shown in Table 17 in a stainless steel cup of a Sorval homogenizer. The homogenate was then refluxed for various times shown in Table 17, cooled to 20° C. and then centrifuged at 10,000 g for 10 min to remove precipitated protein and other insoluble material. The clear supernatant was transferred to a flask and evaporated to 7–8 ml under reduced pressure at 40° C. in a rotary evaporator. The contents of the flask were transferred to a Sep-Pak®C$_{18}$ Solid Phase Extraction Cartridge (Waters). The column was washed with 3×5 ml of 30% methanol and eluted with 4 ×5 ml of methanol. The methanol eluate was dried in a rotary evaporator as above and taken up in 6 ml of distilled water for bioassay using the wheat flour disk method of Xie Y. S., Bodnaryk R. P. and Fields P. G. (1996, Can. Ent. 128:865–875 (1996).

As shown in Table 17, the chloroform removed lipids, pigments and other substances from the air-classified protein rich pea fraction without affecting its activity.

TABLE 17

Efficiency of Various Methods for Extracting Insecticidal Activity from an Air-Classified Protein-Rich Fraction from Peas

| Extraction Method | $EC_{50}$* mg or mg-equivalent per g wheat flour | Units** Extracted per g Starting Material (%) |
|---|---|---|
| Air-Classified Protein-Rich Fraction (Starting Material) | 21.0 (10.4–31.5) | 47.6 (100) |
| Chloroform Extraction | 21.5 (19.6–23.6) | 46.5 (97.7) |
| Water; 20° C. | 178 (95.8–1314) | 5.6 (11.8) |
| Water; reflux 5 min | 374 (242–886) | 2.7 (5.6) |
| Water; reflux 30 min | 367 (272–666) | 2.7 (5.7) |
| 50% Ethanol; 20° C. | 62.5 (45.2–117) | 16.0 (33.6) |
| 50% Ethanol; reflux 5 min | 62.5 (48.1–118) | 16.0 (33.6) |
| 50% Ethanol; reflux 30 min | 64.5 (51.0–127) | 15.5 (32.6) |
| 80% Ethanol; 20° C. | 222 (167–367) | 4.5 (9.5) |
| 80% Ethanol; reflux 5 min | 159 (106–319) | 6.3 (13.2) |
| 80% Ethanol; reflux 30 min | 98.0 (67.6–166) | 10.2 (21.4) |
| 80% Methanol; 20° C. | 74.5 (43.2–125) | 13.4 (28.2) |
| 80% Methanol; reflux 5 min | 23.0 (11.4–34.5) | 43.5 (91.3) |
| 80% Methanol; reflux 30 min | 29.5 (17.7–42.5) | 33.9 (71.2) |
| 80% Methanol; reflux 1 h | 34.5 (22.8–58.3) | 30.0 (60.9) |
| 80% Methanol; reflux 2.5 h | 41.5 (22.8–59.9) | 24.1 (50.6) |

*$EC_{50}$ — Effective concentration causing a 50% reduction in food consumption by *S. oryzae* relative to controls in a wheat disk bioassay (Xie Y. S., et al. Can. Ent. 128:865–875 (1996).
**One unit of insecticidal activity when present in 1 g of wheat flour causes 50% reduction in feeding by *S. oryzae* in a wheat disk bioassay.

Water at 20° C. or at refluxing temperature was not effective in extracting insecticidal activity from the defatted air-classified protein-rich pea fraction (<12% extracted, Table 17).

Ethanol (50%) at 20° C. or at refluxing temperature extracted about one-third of the activity; a higher concentration of ethanol (80%) was less effective (Table 17).

Methanol was effective in extracting activity: refluxing in 80% methanol for 5 min extracted 91.3% of insecticidal activity present in the defatted air-classified protein-rich pea fraction. A lower temperature (20° C.) or longer reflux times (0.5, 1.0, 2.5 h) gave lower recoveries of activity (Table 17).

Since insecticidal activity can be extracted from a defatted air-classified protein rich fraction from peas in high yield by refluxing in 80% methanol for 5 min., this method was pursued in more detail.

Methanol Extraction

One hundred grams of defatted protein-rich pea fraction was added to 2 L of 80% methanol in a 3.8 L stainless-steel Waring blender. The mixture was homogenized at low speed for 1 min and then transferred to a 4 L Erlenmeyer flask. The contents of the flask were stirred magnetically and refluxed for 5 min. The mixture was filtered while hot on a Buchner Funnel fitted with a Whatman No. 1 filter paper. The filtrate was diluted with distilled water to contain <30% methanol. Alternatively, methanol can be removed under reduced pressure at 37° C. to lower its concentration to <30%.

Isolation and Purification: Batch Process

DIAION® HP20AG (100–200 mesh) resin was added to the diluted methanol extract of the air-classified protein rich fraction obtained above (10 g resin per 100 g-equivalent of pea fraction) and the suspension stirred vigorously for 24 h.) The resin was recovered by filtration on a Buchner-type filtering funnel with a coarse porosity (40–60 μm) fritted glass disc and washed with 0.5 L of 30% methanol. Insecticidal activity was eluted from the resin with 0.5 L methanol. Methanol was removed under reduced pressure at 37° C. on a rotary evaporator and the residue taken up in 95% ethanol (1 ml per g-equivalent of pea fraction).

Column Process

A Waters Sept-Pak®Vac $C_8$ cartridge, 20 cc/5 g was conditioned by washing it with 100 ml methanol and then 100 ml distilled water. The diluted methanol extract of the air-classified protein rich fraction from 2.2.1 was pumped onto the cartridge at 15 ml/min with a final loading of 100 g-equivalents of pea fraction per cartridge. The cartridge was washed with 200 ml of 50% methanol. Insecticidal activity was eluted from the cartridge with 500 ml of methanol. Methanol was removed under reduced pressure at 37° C. on a rotary evaporator and the residue taken up in warm 95% ethanol (1 ml per g-equivalent of pea fraction).

Both the batch process using DIAION HP20AG resin and the column process using a Sep-Pak Vac $C_8$ cartridge increased the specific activity of the pea insecticide (Table 18). The specific activity of the insecticide in the air classified protein rich fraction was relatively low (47.6 units/g solids) but after extraction in boiling 80% methanol, isolation and partial purification on DIAION HP20AG or Sept-Pak Vac $C_8$, the specific activities were 1318 and 2085 units/g solids, respectively.

TABLE 18

Efficacy of Various Processes for Isolating Insecticidal Activity From field peas, *P. satiuum*

| Process | Units Recovered per g of Starting Material (% Yield) | Specific Activity Units per g Solids (Purification, fold) |
|---|---|---|
| Air Classification Process | | |
| Protein-rich Fraction* | 47.6 | 47.6 |
| Parrheim Foods | (100) | (0) |
| Batch Process | | |
| DIAION HP20AG | 11.2 | 1318 |

TABLE 18-continued

Efficacy of Various Processes for Isolating Insecticidal Activity From field peas, *P. satiuum*

| Process | Units Recovered per g of Starting Material (% Yield) | Specific Activity Units per g Solids (Purification, fold) |
|---|---|---|
| 100–200 mesh Mitsubishi Column Process | (23.5) | (27.7) |
| Sep-Pak Vac Cartridge $C_8$, 5/g/20 cc Waters | 19.6 (41.2) | 2085 (43.8) |

*The Protein-Rich Fraction served as starting material for the Batch process and Column Process. Activity determined by wheat disk bioassay using *S. oryzae*

Factor(s) responsible for the insecticidal activity of peas can be extracted from an air classified protein-rich pea fraction in boiling 80% methanol, isolated and partially purified in yield and to a high specific activity using a styrene-divinylbenzene copolymer resin, such as Mitsubishi's DIAION HP20AG or a reversed phase $C_8$ cartridge. Batch or column processes can be scaled up and optimized using methods of extraction, isolation and purification that are evident to one of skill in the art.

Peas are treated commercially with alcoholic solvents to remove bitter (Price K. R. and Fenwick G. R. (1984, J. Sci. Food Agric. 35, 887–892) or anti-nutritional substances (Tolman G. H. (1995, Animal Feed Sci. Tech. 56, 159–168). The alcoholic waste products of such processes may serve as a useful feedstock for obtaining pea factors with insecticidal activity. These can be isolated and partially purified from the alcoholic waste using appropriate batch or column processes and resins as described above.

Example 11

Efficacy of the Purified Pea Protein-Rich Fraction

In order to assess the efficacy of the purified pea insecticide for controlling various stored products insects, various doses of the partially purified pea insecticide from the Sep-Pac Vac Cartridge C8 process were prepared by 1:1 serial dilution of a stock solution in 95% ethanol. Doses in 2 ml of 95% ethanol were added dropwise to 100 g of Canadian hard red spring wheat, 16% moisture content in a glass Gem jar. In the case of the rusty grain beetle and red flour beetle, the wheat was supplemented with cracked wheat kernels (5% wt:wt) before insecticide treatment. The jar was sealed and then rotated by hand for 3 min to distribute the dose uniformly on the wheat kernels. A solvent blank was treated with 2 ml of 95% ethanol and handled as above. A control blank was left untreated. The mixtures were then left in the open jars for 24 h at ambient temperature to allow the ethanol to evaporate. Twenty grams of the treated wheat and 10 unsexed stored products insects (20 in the case of the rusty grain beetle) were added to each of five vials 27 min diam×70 mm high (5 replicates). The vials were closed with a screened cap and kept in darkness at 30° C. and 70% relative humidity. After two weeks, adults were removed from vials and counts of living and dead insects were made. The wheat was further incubated for five weeks after which counts of offspring were made.

Regression prediction analysis was used to estimate the $LD_{50}$ and $LD_{95}$, the doses in ppm needed to kill 50% and 95% of adult insects after two weeks and the $EC_{50}$ $EC_5$, the doses in ppm needed to reduce the offspring to 50% and 5% respectively of the control after seven weeks.

Wheat Flour as Carrier

Partially purified insecticide (1 g) in ethanol (25 mls) was added to wheat flour (10 g) and the resultant slurry dried at 50° C. The dried cake was thoroughly ground in a mortar. Various amounts of the insecticide-doped flour were added to 100 g of Canadian hard red spring wheat, mixed by rotation for three minutes and bioassayed against *S. oryzae* and *C. ferrugineus* as described above.

The potency of the air classification protein-rich fraction of peas for *S. oryzae* was relatively low: for adults, the $LD_{50}$ and $LD_{95}$ values were 1350 and 2220 ppm, respectively (Table 20). Partial purification of the insecticide on Sep-Pak Cartridge $C_8$ reduced the $LD_{50}$ and $LD_{95}$ values by as much as 100-fold in some cases. (Table 19).

Adults of the weevils *S. oryzae*, *S. granarius* and *S. zeamis* were most sensitive to the purified insecticide and had the lowest $LD_{50}$ and $LD_{95}$ values. Adults of *C. ferrugineus*, *R. dominica* and *T. castaneum* were insensitive to the insecticide (Table 19).

Offspring production by the weevils was also severely affected by the insecticide. In *T. castaneum* and to a lesser extent *R. dominica* offspring production was also reduced by the insecticide, with $EC_{50}$ values in the same range as found among the weevils. Offspring production by *C. ferrugineus* was virtually unaffected, even by doses 10-fold higher than those given to the other species (Table 19).

Wheat flour doped with purified insecticide was a more effective carrier than ethanol and gave the lowest $LD_{50}$, $LD_{95}$, $EC_{50}$ and $EC_5$ values (Table 19).

TABLE 19

Toxicity (ppm) of a Natural Insecticide Isolated (Air Classification, or Sep-Pac Vac Cartridge, $C_8$) from Field Peas, *P. sativum*, against Various Species of Stored Products Insects Infesting Canada Western Hard Red Spring Wheat. Ethanol or wheat flour was used as a carrier to apply the extract. 95% confidence intervals in parentheses.

| Isolation | Species | Carrier | Adults | | Offspring | |
|---|---|---|---|---|---|---|
| | | | $LD_{50}$ (ppm) | $LD_{95}$ (ppm) | $EC_{50}$ (ppm) | $EC_5$ (ppm) |
| Air Classification | *Sitophilus oryzae* (rice weevil) | none | 1350 (838–2095) | 2220 (1239–6194) | 1430 (1073–3218) | 2450 (1348–8534) |
| Sep-Pak | *S. oryzae* | ethanol | 65 (47–91) | 192 (125–569) | 67 (61–68) | 226 (176–336) |
| | *S. oryzae* | flour | 14 (12–16) | 33 (29–144) | 18 (16–22) | 40 (32–58) |
| | *S. granarius* (granary weevil) | ethanol | 38 (34–41) | 95 (85–124) | 25 (21–28) | 136 (89–156) |
| | *S. zeamais* (maize weevil) | ethanol | 38 (33–42) | 103 (84–126) | 34 (30–40) | 113 (88–155) |
| | *Cryptolestes* | ethanol | >940 | >>940 | >940 | >>940 |

TABLE 19-continued

Toxicity (ppm) of a Natural Insecticide Isolated (Air Classification, or Sep-Pac Vac Cartridge, $C_8$) from Field Peas, *P. sativum*, against Various Species of Stored Products Insects Infesting Canada Western Hard Red Spring Wheat. Ethanol or wheat flour was used as a carrier to apply the extract. 95% confidence intervals in parentheses.

| Isolation | Species | Carrier | Adults | | Offspring | |
|---|---|---|---|---|---|---|
| | | | $LD_{50}$ (ppm) | $LD_{95}$ (ppm) | $EC_{50}$ (ppm) | $EC_5$ (ppm) |
| | *ferrugineus* (rusty grain beetle) | | | | | |
| | *C. ferrugineus* | flour | >940 | >>940 | >940 | >>940 |
| | *Rhyzopertha dominica* (lesser grain borer) | ethanol | >940 | >>940 | 22 (8–37) | 1461 (405–8022) |
| | *Tribolium castaneum* (red flour beetle) | ethanol | >940 | >>940 | 33 (11–58) | 216 (113–3173) |

Purified pea insecticide on a ppm basis is up to 100 times more potent than the air classified protein-rich fraction in controlling adults and offspring production in the weevils *S. oryzae*, *S. granarius* and *S. zeamis*. The purified insecticide is effective in controlling offspring production in the red flour beetle *T. castaneum*, somewhat effective for the lesser grain borer, *R. dominica* and not effective for the rusty grain beetle, *C. ferrugineus*.

Example 12

The Pea Insecticidal Fraction is Not Comprised of Lectin or Trypsin Inhibitor

Lectins and trypsin inhibitors shown in Table 20 were assayed in their native form to determine their activity against *S. oryzae* in the wheat flour disk bioassay. Compounds that showed significant activity were processed in a manner identical to that used for the extraction, isolation and partial purification of the pea insecticide as detailed in Example 10.

Pea lectin, pea trypsin inhibitor and concanavalin A at high concentrations (1% w/w, 10,000 ppm) were weakly active against *S. oryzae* in the wheat flour disk feeding bioassay. No activity was detected after the compounds were refluxed in 80% methanol for 5 min and chromatographed on a $C_{18}$ matrix (Table 20).

Trypsin inhibitor from soya bean and lima bean were inactive when bioassayed against *S. oryzae* and were not further studied.

Pea lectin, pea trypsin inhibitor and concanavalin A are weakly active against *S. oryzae*, a finding that is not surprising in view of reports that plant lectins (Hepher, A., Edwards, G. A. and Gatehouse, J. A. (1989), European Patent Application, Publication number: 0 351 924 A2); Murdock, L. L., Huesing J. E., Nielsen S. S., Pratt R. C. and Shade R. E. (1990, Phytochemistry 29, 85–89; Rahbe Y., Sauvion N., Febvay G., Peumans W. J. and Gatehouse A. M. R. (1995), Entomol. Exp. Appl. 76, 143–155; Peumans W. J. and Van Damme E. J. M. (1995, Plant Physiol. 109, 347–352) and proteinase inhibitors (Broadway, R. M., Duffey S. S., Pearce, G. and Ryan C. A. (1986, Entomol. Exp. Appl. 41, 33–38; Gatehouse, A. M. R., Shi Y., Powell K. S., Brough C., Hilder V. A., Hamilton W. D. O., Newell, C. A., Merryweather A., Boulter, D. and Gatehouse, J. A. (1993, Phil. Trans. R. Soc. Lond. B 342, 279–286) can affect insects adversely. However, neither lectins nor protease inhibitors are responsible for the insecticidal activity of the partially purified pea extract because they do not survive the conditions used to extract and purify the pea insecticide characterized herein.

TABLE 20

Effect of Lectins and Trypsin Inhibitors on the Feeding Rate of *S. oryzae*

| Compound Tested* | Feeding Rate (% of Control) |
|---|---|
| Partially purified pea insecticide obtained by refluxing pea flour in 80% methanol for 5 min followed by chromatography on a $C_{18}$ matrix | 9.4 |
| Pea lectin | 71.4 |
| Pea lectin refluxed in 80% methanol for 5 min, then chromatographed on a $C_{18}$ matrix | 101.0 |
| Wheat germ lectin | 88.6 |
| Concanavalin A | 82.5 |
| Concanavalin A refluxed in 80% methanol for 5 min, then chromatographed on a $C_{18}$ matrix | 99.0 |
| Pea trypsin inhibitor | 35.4 |
| Pea trypsin inhibitor refluxed in 80% methanol for 5 min, then chromatographed on a $C_{18}$ matrix | 99.8 |
| Soybean trypsin inhibitor | 98.7 |
| Lima bean trypsin inhibitor | 96.2 |

*Compounds tested at 1% w/w in a wheat flour disk bioassay (Xie Y. S., Bodnaryk R. P. and Fields P. G. (1996). A rapid and simple flour disk bioassay for testing natural substances active against stored-product insects. Can. Ent. 128: 865–875 (1996).

Example 13

Insecticidal Activity of Other Legumes

Seeds of the legumes in Table 21 were obtained from Dr. Tom Warkentin, Agriculture and Agri-Food Canada, Morden Research Centre, Morden Manitoba and Dr. Andre Morin, Agriculture and Agri-Food Canada, Food Research and Development Centre, St. Hyacinthe, Quebec. Seeds were milled in a Braun coffee mill and the activity of the flour was bioassayed against *S. oryzae* using the wheat flour disk method (Xie Y. S., Bodnaryk R. P. and Fields P. G. (1996, Can. Ent. 128: 865–875 (1996).

All of the legume seeds in Table 21, were inactive or weakly active when bioassayed against *S. oryzae* with the exception of certain lentils; *Lens culinaris* cv Eston was highly active but *Lens culinaris* cv Laird was almost inactive. The brown-and-orange-seeded lentils were active, but the green-seeded lentil showed only weak activity (Table 21).

TABLE 21

Insecticidal Activity in the Seeds of
Various Legumes Against *S. oryzae*

| Species | $EC_{50}$, mg/g (95% confidence interval) |
|---|---|
| *Pisum sativum* cv. AC Tamor | 17.0 (14.3–22.2) |
| *Arachis hypogea* | n/a |
| *Cajanus cajan* | 106 (81.6–176) |
| *Cicer arietinum* | n/a |
| *Lablab purpureus* | 120 (85.0–190) |
| *Lens culinaris* cv. Eston | 26.0 (19.6–37.5) |
| *L. culinaris* cv. Laird | 214 (154–367) |
| *L. culinaris* cv. brown seeded | 35.3 (29.2–41.4) |
| *L. culinaris* orange seeded | 30.0 (21.9–40.9) |
| *L. culinaris* green seeded | 80.0 (68.7–99.0) |
| *Lupinus albus* cv Bitter Shinfield 27E3016 | n/a |
| *L. albus* cv. Ultra (Elliot) | n/a |
| *L. angustifolius* cv. Gungurru | n/a |
| *Macrotyloma uniflorum* | 147 (121–217) |
| *Phaseolus limensis* | n/a |
| *P. lunatus* | n/a |
| *P. vulgaris* navy bean cv. T9006 | 125 (96.0–149) |
| *P. vulgaris* pinto bean cv. Othello | 169 (152–187) |
| *P. vulgaris* dark red kidney bean cv. Moncalm | 134 (66.1–179) |
| *Psophocarpus tetragonolobus* cv Chimbu | 156 (125–184) |
| *P. tetragonolobus* cv. TPF2 | 140 (56.2–195) |
| *Vignia angularis* | n/a |
| *V. anonitafolia* | 110 (71.3–179) |
| *V. faba* | 246 (176–429) |
| *V. mungo* | 83.4 (71.7–103) |
| *V. radiata* | n/a |
| *V. unguiculata* | 137 (119–160) |

*$EC_{50}$ dose required to reduce feeding by 50% of controls in a wheat disc bioassay (Xie Y. S., Bodnaryk R. P. and Fields P. G. (1996). A rapid and simple flour disk bioassay for testing natural substances active against stored-product insects. Can. Ent. 128: 865–875 (1996)
n/a = not active The seeds of most legume species do not exhibit insecticidal activity as described for peas, with the exception of lentils. We report here that certain lentils are also a good source of insecticidal activity.

Example 14

Insecticidal Activity Against Indian Meal Moth and Flea Beetle

Indian meal moth

Pea extract was applied to whole wheat kernels at 0, 23.5, 47, 94, 188 and 376 ppm. The pea extract was partially purified from Parrheim's protein-rich, air classified fraction on a Sep-Pac C8 Cartridge as previously described. The purification steps are: defat protein-rich fraction with chloroform, extract insecticide in 80% boiling methanol for 5 minutes, filter, pump filtrate onto a C8 Sep-Pac Vac 20 cc cartridge, wash with methanol, wash with 50% methanol, elute insecticide with methanol, evaporate methanol, dissolve residue in warm 95% ethanol.

Indian meal moth were placed on the grain as either eggs or larvae (10 individuals/vial, 20 g wheat/vial, 5 replicates/concentration) and held at 25±1° C., 75% RH, 16 h light: 8 h dark. The number and the date of adults emerged was noted. From the preliminary data it is evident that the pea extract does not greatly increase mortality. The Indian meal moth is not as sensitive as Sitophilus spp which have a $LD_{95}$ of 33 to 180 ppm.

Flea Beetles

Pea extract was tested against flea beetles (*Phyllotreta cruciferae* (Goeze)), a pest of canola in western Canada that causes $ 20–100 million damage annually. A leaf disk bioassay was used to determine anti-feedant activity. Pea extract was prepared as above. There were two trials, one with concentrations from 0, 89, 178, 356 μg pea extract/leaf disk $cm^2$, and the other with 0, 1.1, 4.5 and μg pea extract/leaf disk $cm^2$. Leaf disks were 0.82 cm in diameter and cut from canola cv Excel cotyledons. Two leaf disks were taken from each cotyledon, and used as a pair in the test. The pair of leaf disks were placed in a petri dish (60 mm diameter), which had a 1% agar solution with 20:20:20 fertiliser with micronutrients under a filter paper. This allows the leaf disks to be moist and grow slightly, yet does not hinder the movement of flea beetles. Forty μl of test solution (pea extract dissolved in ethanol) was placed on one of the leaf disks, and 40 μl of ethanol on the other leaf disk. Five flea beetles were introduced into the petri dish. Percent feeding damage was estimated visually after 3 and 5 days, as a percentage of the leaf disk surface consumed (0 to 10, where 10 is the whole disk). After five days the mortality of the flea beetles was noted and the dry weights of the leaf disks taken. There were 20 replicates per dose.

At 17.8 μg pea extract/leaf disk $cm^2$ there was a significant reduction in the amount of the leaf disk consumed. At the higher concentrations of 89 to 356 μg pea extract/leaf disk $cm^2$ no dose response was observed as was seem at the lower concentrations. This is probably because 89 μg pea extract /leaf disk $cm^2$ elicits the maximum response. There was no significant increase in mortality with pea extract dose. The results are shown below in Table 22.

TABLE 22

The effects of pea extract on the flea beetle feeding on canola leaf disks (mean ± SEM)

| Dose ($\mu$g/$cm^2$) | Consumed after 3 days (%) | | Consumed after 5 days (%) | | Dry weight of leaf disks after 5 days (mg) | | Mortality (%) |
|---|---|---|---|---|---|---|---|
| | control | treated | control | treated | control | treated | |
| 0 | 40 ± 6 | 37 ± 7 | 52 ± 6 | 46 ± 6 | 1.4 ± 0.2 | 1.3 ± 0.2 | 17 |
| 1.1 | 43 ± 5 | 38 ± 6 | 51 ± 5 | 48 ± 6 | 1.3 ± 0.2 | 1.4 ± 0.2 | 8 |
| 4.5 | 40 ± 5 | 32 ± 6 | 50 ± 5 | 42 ± 6 | 1.4 ± 0.2 | 1.4 ± 0.2 | 5 |
| 17.8 | 43 ± 6 | 17 ± 4 | 54 ± 6 | 29 ± 4 | 1.2 ± 0.2 | 1.9 ± 0.2 | 6 |
| 0 | 20 ± 4 | 19 ± 3 | 43 ± 4 | 39 ± 3 | 1.7 ± 0.1 | 1.8 ± 0.1 | 3 |
| 89 | 27 ± 4 | 4 ± 1 | 49 ± 5 | 14 ± 1 | 1.5 ± 0.1 | 2.1 ± 0.1 | 8 |
| 178 | 16 ± 3 | 7 ± 1 | 37 ± 3 | 15 ± 2 | 1.9 ± 0.1 | 2.2 ± 0.1 | 9 |
| 356 | 29 ± 5 | 4 ± 1 | 57 ± 6 | 13 ± 2 | 1.0 ± 0.1 | 1.9 ± 0.1 | 8 |

Note: without flea beetles, disk dry weights were for low concentration trial, control 2.6 ± 0.1 and ethanol 2.6 ± 0.1, for high concentration trial control 2.5 ± 0.1 and ethanol 2.7 ± 0.1

Example 15

Grasshopper Feeding Trial

Pea extract in 95% ethanol (10 mg refined extract/ml EtOH) was applied to 12 mm canola (AC Excel) leaf disks (8 μl). The solution was allowed to evaporate before the leaf disks were presented to the grasshoppers. This gave a concentration of 71 ug of refined pea extract/cm$^2$. As a control 95% ethanol was also applied to some leaf disks. The experiment was set up as a RCBD (3 blocks with 3 representatives in each block). Individual leaves served as blocks.

Second instar grasshoppers *Melanoplus sanguinipes* (F.) were placed in 8 dram vials (one grasshopper per vial) and starved for 3 hours and then presented with a leaf disk. Grasshoppers were allowed to feed for a period of 4 hours. Leaf disks were dried at 60° C. for 12 hours. Dry weight were measured.

Dry weights for leaf disks treated with pea extract (0.0011 gms) were significantly greater than disks treated with ethanol only (0.0011) (P=0.0017). These results demonstrate the effectiveness of the pea extract against grasshoppers.

Example 16

Insecticidal Activity Against Larvae of Bertha armyworm and Diamondback Moth Canola leaf disks (12 mm diameter) were treated as follows:

Treatment 1 PE=Pea extract on canola disks in 95% EtOH (presented to insects) 10 mg extract/ml EtOH Treatment 2 CNP=95% ETOH on disks (Control, not presented to insects); and Treatment 3 CP=95% ETOH on disks (Control, presented to insects).

A separate experiment was conducted for each species. The experiment was set up as a RCBD (4 blocks with 5 reps (i.e. individual insects) in each block). Individual leaves (*B. napis* cv. AC Excel) served as blocks (one large, lower leaf from 4 different plants).

Eight microliter volumes were applied to 12 mm leaf disks. The solution was allowed to evaporate before the leaf disks were presented to the insects. This gave a concentration of 71 μg of refined pea extract/cm$^2$.

Fourth instar insects were placed in 8 dram vials (one insect per vial) and starved for 3.5 hours and then presented with a leaf disk. Insect wts. were determined just prior to being given leaf disks. Insects were allowed to feed for a period of 3.5 hours. One set of leaf disks were not presented to the insects.

Leaf disks were dried at 60° C. for 12 hours. Dry weights were determined.

Bertha armyworm *Mamestra configurata* Wlk.

The model was significant (P=0.0090) with a CV of 4.22 and a R$^2$=0.88; treatments were significant (P=0.0030). The results for the Waller-Duncan K-ratio T test (and mean values) are as follows (T=treatment).

| Waller grouping | Mean (mg) | Treatment | % Consumed |
|---|---|---|---|
| A | 2.3 | CNP | |
| A | 2.2 | PE | 4.3 |
| B | 1.9 | CP | 17.4 |

The results suggest that the pea extract significantly suppresses feeding in bertha armyworm larvae.

Diamondback Moth *Plutella xylostella* (L.)

Treatments were significant (P=0.0030). The results for the Waller-Duncan K-ratio T test (and mean values) are as follows (T=treatment).

| Waller grouping | Mean (mg) | Treatment | % Consumed |
|---|---|---|---|
| A | 2.2 | PB | |
| AB | 2.1 | CNP | 4.5 |
| B | 1.9 | CP | 13.6 |

The results suggest that the pea extract significantly suppresses feeding in diamondback larvae.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiments of the invention in which an exclusive property or privilege is claimed are defined as follows:

1. A composition which is effective in controlling insect pests comprising the protein-rich fraction of a legume extract which is alcohol soluble, protease sensitive and has a molecular weight of <4000 daltons and wherein said legume is selected from the group consisting of species from the genus Pisum, *Cajanus cajan, Lablab purpureus, Lens culinaris, Macrotyloma uniflorum, Phaseolus vulgaris, Psophocarpus tetragonolobus, Vignia anonitafolia, Vignia faba, Vignia mungo* and *Vignia unguiculata*.

2. The composition of claim 1 wherein an effective concentration of the protein-rich fraction for the treatment of grains or flours is from 0.001% to 10% weight/weight.

3. The composition of claim 1 wherein an effective concentration of the protein-rich fraction for the treatment of plants is from 17 μg to 90 μg per cm$^2$.

4. The composition of claim 1 wherein the protein-rich fraction is applied as a powder or in an aqueous medium.

5. The composition of claim 1 wherein the insect pests are selected from the group consisting of rice weevil, maize weevil, granary weevil, rusty grain weevil, flat grain beetle, flour mill beetle, red flour beetle, confused flour beetle, lesser grain borer, Indian meal moth, flea beetle, grasshopper, bertha armyworm and diamondback moth.

6. A method of preparing the composition of claim 1 comprising subjecting the protein-rich fraction to a combination of ammonium sulphate precipitation followed by ion-exchange and gel filtration chromatography.

7. A method of obtaining the composition of claim 1, comprising extracting the legume seeds using at least one solvent.

8. The method of claim 7 wherein the solvent is selected from the group consisting of chloroform, methanol, ethanol, or a combination thereof.

9. The method of claim 8 wherein the solvent used is a combination of chloroform and methanol.

10. The method of claim 9 wherein the composition is further purified using either a styrene-divinylbenzene copolymer resin or reverse phase chromatography.

11. The composition of claim 1 wherein the legume is *Pisum sativum*.

12. The composition of claim 1 wherein the legume is *Lens culinaris*.

13. A method of controlling insect pests comprising exposing said insect pests to an effective amount of the composition of claim 1.

* * * * *